US011285077B2

(12) United States Patent
Tagawa et al.

(10) Patent No.: US 11,285,077 B2
(45) Date of Patent: Mar. 29, 2022

(54) BLOOD COLLECTION DEVICE, BLOOD COLLECTION SET, BLOOD COLLECTION METHOD

(71) Applicant: Sysmex Corporation, Kobe (JP)

(72) Inventors: Ayato Tagawa, Kobe (JP); Junko Kojima, Kobe (JP); Nobuyasu Hori, Kobe (JP); Kenji Akama, Kobe (JP); Masaya Okada, Kobe (JP); Kunpeng Cai, Kobe (JP); Samiko Hosoya, Kobe (JP); Shigeki Iwanaga, Kobe (JP)

(73) Assignee: SYSMEX CORPORATION, Hyogo (JP)

(*) Notice: Subject to any disclaimer, the term of this patent is extended or adjusted under 35 U.S.C. 154(b) by 713 days.

(21) Appl. No.: 15/653,816

(22) Filed: Jul. 19, 2017

(65) Prior Publication Data

US 2018/0021219 A1    Jan. 25, 2018

(30) Foreign Application Priority Data

Jul. 22, 2016  (JP) .............................. JP2016-144503

(51) Int. Cl.
*A61J 1/14*         (2006.01)
*B01L 3/00*         (2006.01)
(Continued)

(52) U.S. Cl.
CPC ............. *A61J 1/1475* (2013.01); *A61B 5/155* (2013.01); *A61B 5/150022* (2013.01); *A61B 5/15105* (2013.01); *A61B 5/150358* (2013.01); *A61B 5/150755* (2013.01); *A61B 5/150969* (2013.01); *A61J 1/05* (2013.01); *A61J 1/165* (2013.01);
(Continued)

(58) Field of Classification Search
CPC ..... A61J 1/1475; A61J 1/05; A61B 5/150022; A61B 5/150358; A61B 5/150755; A61B 5/150969; A61B 5/15105; A61B 5/155; A61B 5/150412; A61B 5/150748; B01L 3/502715; B01L 3/5082; F28D 15/0233
See application file for complete search history.

(56) References Cited

U.S. PATENT DOCUMENTS 5,938,679 A      8/1999  Freeman et al.
9,623,411 B1 *   4/2017  Frenzel ............... B01F 11/0074
(Continued)

FOREIGN PATENT DOCUMENTS

CN     2203869 Y     7/1995
CN     1527937 A     9/2004
(Continued)

OTHER PUBLICATIONS

The Japanese Office Action dated Jan. 14, 2020 in a counterpart Japanese patent application No. 2016-144503.
(Continued)

*Primary Examiner* — Patrick Fernandes
(74) *Attorney, Agent, or Firm* — Crowell & Moring LLP

(57) ABSTRACT

A blood collection device including a flow path to flow blood by capillary action capable of collecting a large amount of blood is provided. The blood collection device includes an introduction inlet 23 for introducing the blood of the subject M, a substrate 20 connected to the introduction inlet 23 and including a flow path 25 to flow the blood by capillary action, and a cooling body 30 for cooling the flow path 25.

19 Claims, 35 Drawing Sheets

(51) Int. Cl.
*A61B 5/151* (2006.01)
*A61B 5/15* (2006.01)
*A61B 5/155* (2006.01)
*A61J 1/05* (2006.01)
*A61J 1/16* (2006.01)

(52) U.S. Cl.
CPC ... *B01L 3/502715* (2013.01); *A61B 5/150412* (2013.01); *A61B 5/150748* (2013.01); *B01L 3/5082* (2013.01); *B01L 2200/0684* (2013.01); *B01L 2300/024* (2013.01); *B01L 2300/069* (2013.01); *B01L 2300/0672* (2013.01); *B01L 2300/0851* (2013.01); *B01L 2300/0864* (2013.01); *B01L 2300/161* (2013.01); *B01L 2300/1822* (2013.01); *B01L 2300/1894* (2013.01)

(56) References Cited

U.S. PATENT DOCUMENTS

| | | |
|---|---|---|
| 2004/0171968 A1 | 9/2004 | Katsuki et al. |
| 2005/0033197 A1* | 2/2005 | Cottler ................ A61M 1/0058 600/573 |
| 2005/0106713 A1 | 5/2005 | Phan et al. |
| 2006/0147343 A1 | 7/2006 | Teramoto |
| 2007/0245810 A1* | 10/2007 | Carter ................ C07D 207/46 73/53.01 |
| 2009/0305407 A1* | 12/2009 | Temple ................ G01N 1/14 435/372 |
| 2010/0049126 A1 | 2/2010 | Bronfeld et al. |
| 2010/0174211 A1* | 7/2010 | Frey ................ A61B 5/150358 600/583 |
| 2011/0088413 A1* | 4/2011 | Lampe ................ F28D 15/0233 62/68 |
| 2011/0118568 A1 | 5/2011 | Sei |
| 2011/0137143 A1 | 6/2011 | Fukuda et al. |
| 2013/0211289 A1 | 8/2013 | Moga et al. |
| 2014/0234949 A1* | 8/2014 | Wasson ............ G01N 35/00871 435/287.2 |

FOREIGN PATENT DOCUMENTS

| | | |
|---|---|---|
| CN | 1809754 A | 7/2006 |
| CN | 1874720 A | 12/2006 |
| CN | 101790350 A | 7/2010 |
| CN | 203053750 U | 7/2013 |
| CN | 203953675 U | 11/2014 |
| CN | 204815040 U | 12/2015 |
| CN | 105913170 A | 8/2016 |
| JP | H07-95975 A | 4/1995 |
| JP | 2002-350432 A | 12/2002 |
| JP | 3853789 B2 | 12/2006 |
| JP | 2011-045450 A | 3/2011 |
| JP | 2017-187358 A | 10/2017 |
| WO | 2010/013598 A1 | 2/2010 |

OTHER PUBLICATIONS

The Chinese Office Action dated Oct. 21, 2020 in a counterpart Chinese patent application No. 201710564594.2.

\* cited by examiner

BLOOD COLLECTION DEVICE, BLOOD COLLECTION SET, BLOOD COLLECTION METHOD

CROSS REFERENCE TO RELATED APPLICATIONS

This application claims priority from prior Japanese Patent Application No. 2016-144503, filed on Jul. 22, 2016, entitled "BLOOD COLLECTION DEVICE, BLOOD COLLECTION SET, BLOOD COLLECTION METHOD", the entire contents of which are incorporated herein by reference.

FIELD OF THE INVENTION

The present invention relates to a blood collection device, blood collection set, and blood collection method for collecting blood from a subject.

BACKGROUND

Generally, a method in which a hollow needle is inserted into a blood vessel and blood drawn into a blood collection tube is used as a method of collecting blood from the skin of a subject for a blood test or the like. Although this method is capable of collecting a large amount of blood, it is accompanied by painfulness of the subject.

Conversely, Patent Reference 1 discloses a device for collecting blood from capillaries in a subcutaneous tissue so as to enable minimally invasive blood collection. As shown in FIGS. 33 and 35, for example, this device includes a main body 101 having an inner space 102, a plunger 103 inserted into the inner space from one end side of the main body 101, and a base 104 mounted at the other end side of the main body 101. As shown in FIG. 34, a flow path 105 for flowing blood by a capillary phenomenon, an opening 106 connected to one end of the flow path 105, and a detection area 107 connected to the other end of the flow path 105 are formed in the based 104. As shown in FIG. 33, a fine needle 108 is provided in alignment with the position of the opening on the surface of the plunger 103 on the side of the base 104.

The device of patent reference 1 is configured, as schematically shown in FIG. 35, so that the skin of the subject is punctured by the subject him/herself pushing the plunger 103 through the opening 106 when the base 104 in contact with the skin of the subject, and blood flowing from the skin is introduced into the opening 106 of the base 104. The blood introduced into the opening 106 flows through the flow path 105 by capillary phenomenon and is transported to the detection area 107.

PRIOR ART DOCUMENTS

Patent Documents

[Patent Reference 1] United States Patent Publication No. 2013/0211289

SUMMARY OF THE INVENTION

The device disclosed on patent reference 1 only considers collecting a trace amount of blood of approximately several 1 µL to several hundred pt. However, blood testing may require, for example, 1 mL or more of blood.

As a result of repeated study of blood collection devices capable of recovering more blood, the inventors of the present application have learned that although collection of 1 mL or more of blood using the device described in patent reference 1 was attempted, the blood coagulated while blood was flowing through the flow path using the capillary phenomenon gave rise to the phenomenon of flow path obstruction. Then, it was found that suppression of coagulation of the blood in the flow path is important for recovering more blood, and the following invention was completed.

The blood collection device of the present invention includes an introduction inlet for introducing the blood of the subject, a substrate connected to the introduction inlet and including a flow path to flow the blood by capillary action, and a cooling body for cooling the flow path.

Since the blood collection device of the above configuration has a cooling body for cooling the flow path, it is possible to suppress coagulation of the blood in the flow path. The flow path therefore is not blocked by coagulated blood, and blood can continuously flow within the flow path. Accordingly, more blood can be collected by the blood collection device.

Note that the shape, size and the like of the introduction inlet are arbitrary as long as blood can be introduced into the blood collection device, and the introduction inlet can be formed as a round hole shape, a rectangular hole shape or the like. The flow path also can be formed into an arbitrary shape such as a tube shape, a hole shape, a groove shape, and the like as long as blood can flow by capillary action. The groove width, groove depth, and length in the case of a groove shape, and the diameter and length in the case of a tube shape or hole shape flow path, also may be arbitrary, insofar as capillary action is promoted.

The cooling body cools the flow path, thereby cooling the blood in the flow path to a temperature at which coagulation is suppressed, for example, the cooling body cools the blood to a temperature lower than human body temperature. Further, a cooling body capable of continuously cooling the flow path for a time during which a desired amount of blood can be collected is utilized.

The blood collection method of the invention includes
a step of fixing a blood collection instrument that has a flow path for allowing blood to flow by capillary action to the skin of a subject;
a step of introducing blood flowing out of the skin into the blood collection instrument; and
a step of flowing the introduced blood into the flow path by cooling the flow path.

According to the present invention, it is possible to recover more blood while suppressing coagulation of blood in the blood collection device having a flow path for allowing blood to flow by capillary action.

BRIEF DESCRIPTION OF THE DRAWINGS

FIG. 1 is a perspective view of the blood collection set of the invention, wherein

DESCRIPTION OF THE EMBODIMENTS OF THE INVENTION

Figure 1A:
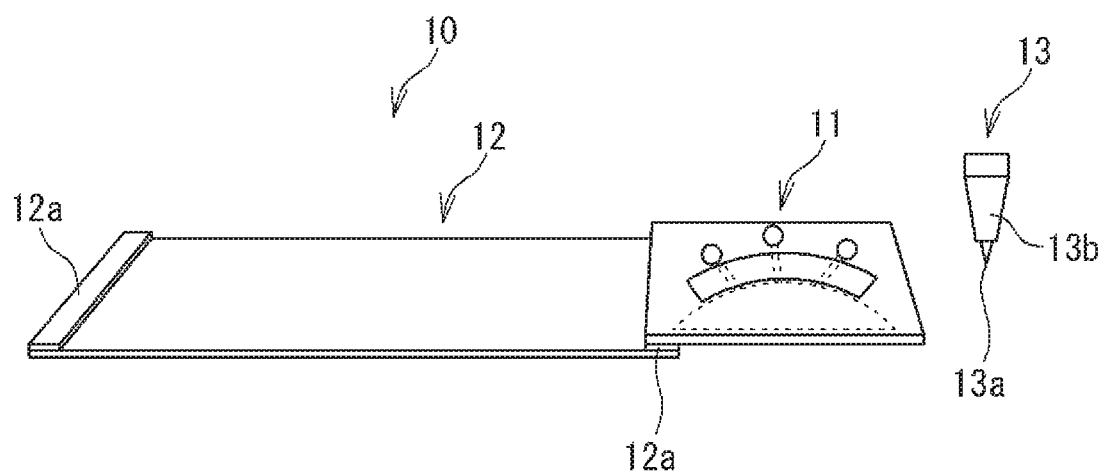
FIG. 1A shows the fixing tool 12 in the expanded state.

The embodiments of the invention are described hereinafter referring to the drawings.

Figure 1B:
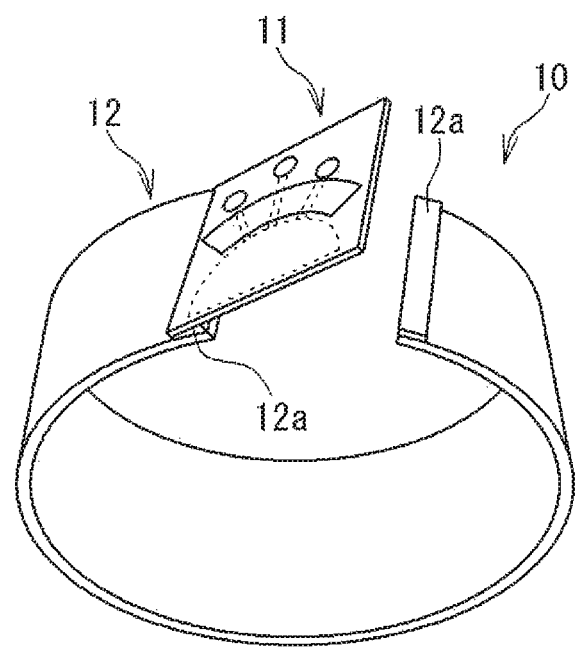
FIG. 1B shows the fixture 12 in the curved state.
Figure 2:
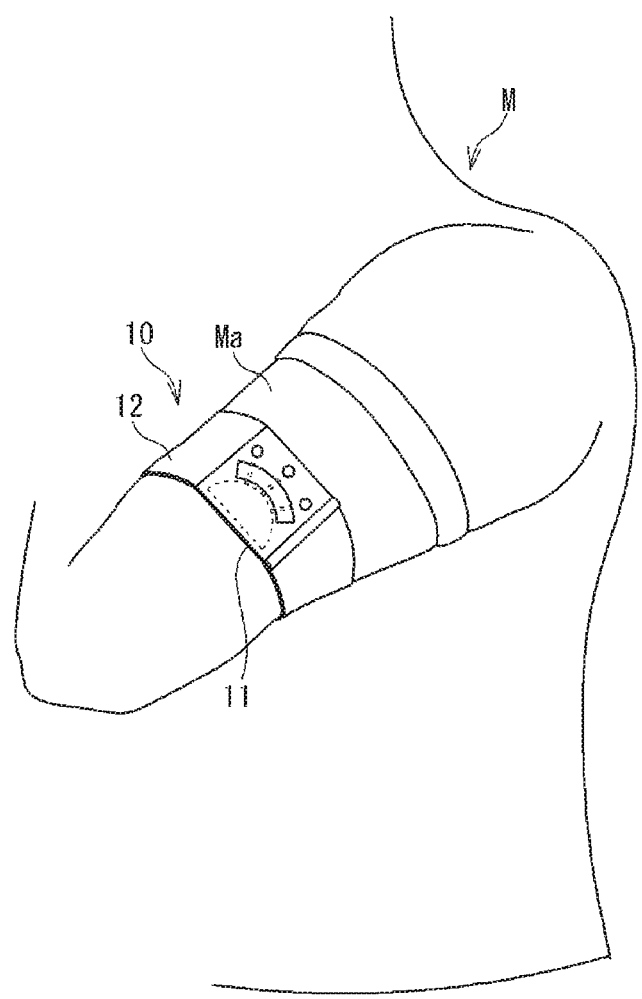
FIG. 2 is a perspective view showing the blood collection set attached on a subject.

As shown in FIGS. 1 and 2, the blood collection set 10 of the embodiment makes it possible to perform blood sampling by the subject himself with low invasiveness. Therefore, for example, the blood collection set 10 can be suitably used by a blood testing service for conducting a blood test without visiting a hospital by sending blood collected by the subject himself at home to the examining facility. Also, in recent years, there has been research on an examination called "liquid biopsy", which performs an examination with performance equivalent to that of biopsy done by collecting some living tissue, such as a tumor, using the subject's blood or body fluid, and the blood collection set 10 according to the embodiment can collect an amount necessary for such examination, for example, about 1 mL of blood.

The blood collection set 10 includes a blood collection device 11, a fixing tool 12, and a puncture tool 13. The blood collection device 11 is used for collecting and storing the blood flowing from the skin of the subject M. The fixing tool 12 is used to fix the blood collection device 11 to the skin of the subject M. The puncture tool 13 is used for forming fine holes in the skin of the subject M and allowing blood to flow out from the holes. Specific configurations are described below.

Structure of the Blood Collection Device

Figure 3:
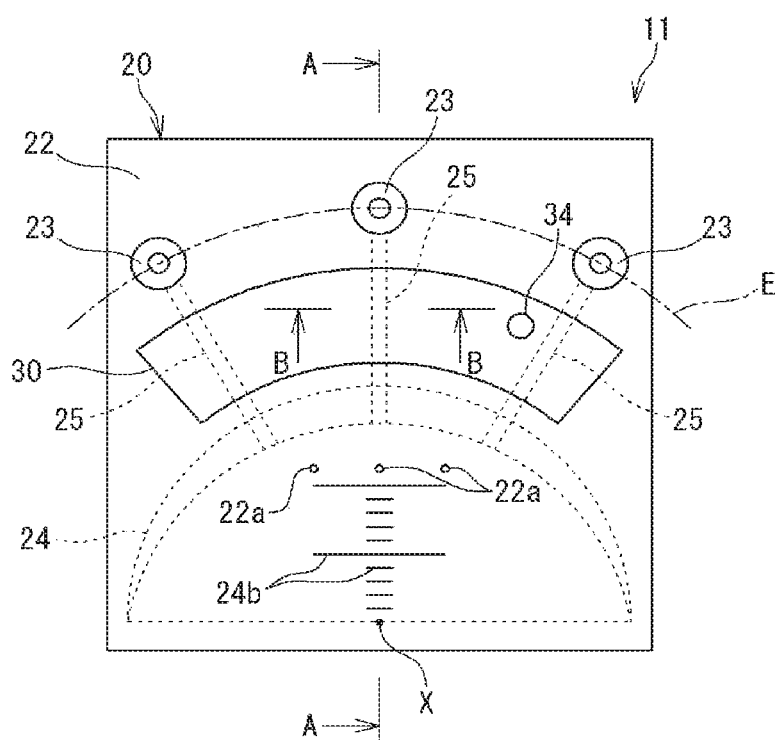
FIG. 3 is a plan view of the blood collection device.
Figure 4:
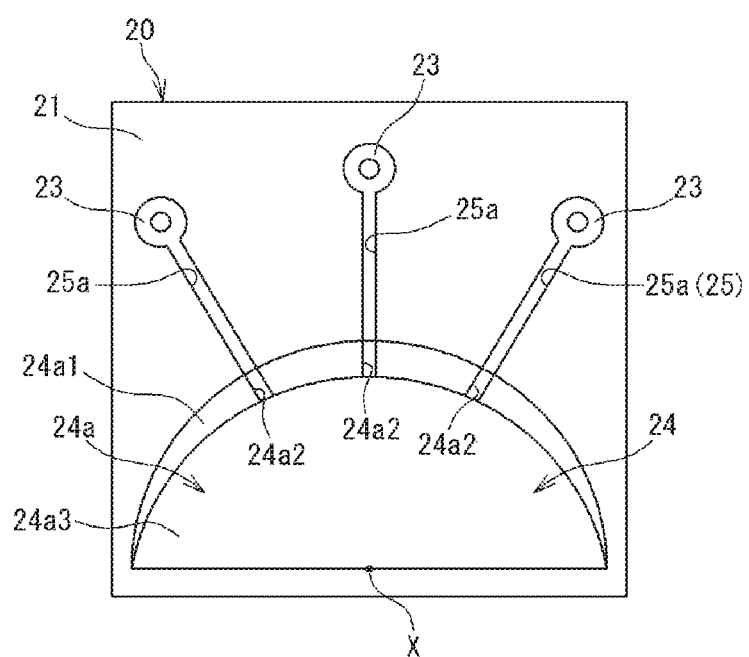
FIG. 4 is a plan view of a main body part of the substrate of the blood collection device.
Figure 5:
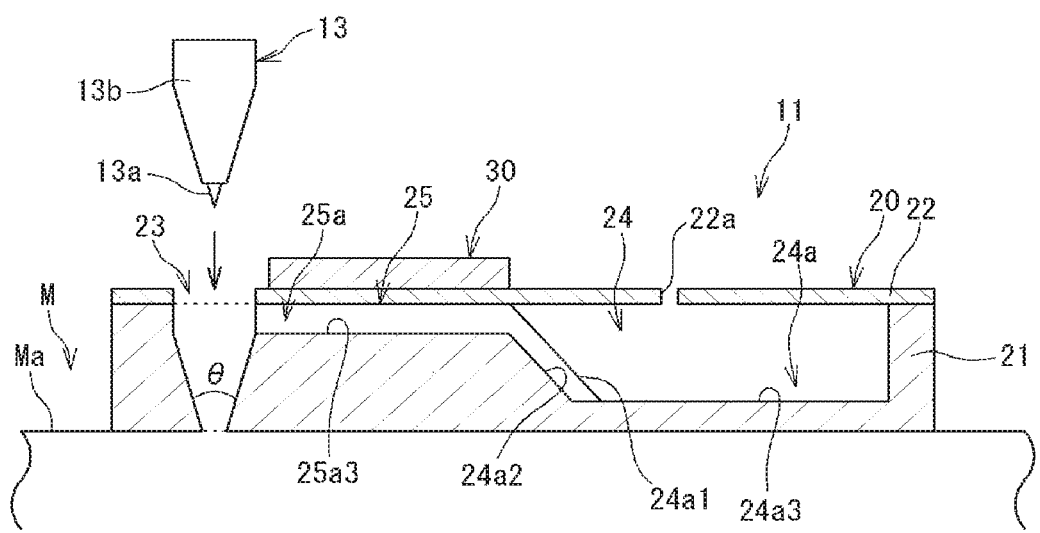
FIG. 5 is an A-A cross sectional view of FIG. 3.

As shown in FIG. 3, the blood collection device 11 includes a substrate 20, and a cooling body 30. The substrate 20 is formed in a square thin plate shape such as a square or a rectangle in plan view. For example, the substrate 20 has a planar shape that is a square shape of about 30 mm×30 mm and a thickness of about 5 mm. The direction perpendicular to the paper surface in FIGS. 3 and 4, and the vertical direction in FIG. 5, are described as the vertical direction of the blood collection tool 11 in the following description. The dimensions of the substrate 20 are illustrative and are not particularly limited.

As shown in FIG. 5, the substrate 20 is fixed to the subject M in a state in which its lower surface side is in contact with the skin Ma of the subject M. The substrate 20 is formed of a flexible synthetic resin material in order to increase adhesion to the skin Ma of the subject M. For example, the substrate 20 is formed of polymethyl methacrylate, cycloolefin copolymer, polycarbonate, cycloolefin polymer, polystyrene or the like. More preferably, the substrate 20 is formed of polymethyl methacrylate and poly (2-methoxyethyl acrylate).

The substrate 20 has a main body part 21 and a cover part 22. As shown in FIGS. 3 and 4, the main body art 21 and the cover part 22 are formed in substantially with the same square shape in plan view. As shown in FIG. 5, the cover part 22 is adhered while in a state of overlapping the upper surface of the main body part 21. The main body part 21 has a thickness that occupies most of the thickness of the substrate 20. The cover part 22 is formed in a sheet shape that is thinner than the main body part 21. The substrate 20 may be formed transparent or translucent, or it may be formed opaque. When the substrate 20 is transparent or translucent, it becomes possible to confirm the collected blood from the outside.

An introduction inlet 23, a reservoir part 24, and a flow path 25 are formed on the substrate 20. The introduction inlet 23 is used to introduce blood flowing out from the skin Ma of the subject M into the blood collection device 11. The introduction inlet 23 is configured by a hole passing through the substrate 20 in the vertical direction, that is, in the thickness direction. The introduction inlet 23 is formed to have a larger opening area on the upper side and a smaller opening area on the lower side, and the inner surface is inclined from the upper side to the lower side. In the embodiment, the upper end part of the introduction inlet 23 is formed in a cylindrical shape, and the lower side from the cylindrical part is formed in a substantially conical shape having an inner diameter that is larger toward the upper side. As shown in FIG. 3, the substrate 20 of the embodiment has introduction inlets 23 formed at three positions. Each introduction inlet 23 is formed at equal intervals on a virtual circle E centered on a point X virtually set on one side part of the substrate 20. Three introduction inlets 23 are formed near the other side of the substrate 20 on the side opposite the side of the substrate 20 where the point X is set.

As shown in FIG. 5, the diameter of the lower end part of the introduction inlet 23 can be set within a range of 0.5 mm or more and 2.0 mm or less, preferably 0.8 mm or more and 1.8 mm or less, more preferably 1.0 mm or more and 1.5 mm or less. In the present embodiment, the diameter is 1.0 mm. Further, the vertex angle (taper angle) 0 of the conical shape of the introduction inlet 23 can be set to 45° or less, preferably 5° or more and 30° or less, and more preferably 10° or more and 15° or less.

The reservoir part 24 is used to store the blood introduced into the blood collection device 11 from the introduction inlet 23. The reservoir part 24 includes a concave part 24a formed on the upper surface of the main body part 21. The reservoir part 24 is configured by covering the upper part of the concave part 24a of the main body part 21 with the cover part 22. The storage unit 24 has a capacity of 1 mL or more and 5 mL or less. Since the reservoir part 24 has a capacity of 1 mL or more, the stored blood can be subjected to many items of blood test, and can also be used for the aforementioned liquid biopsy. Note that the capacity of the reservoir part 24 can be increased or decreased by changing the thickness of the substrate 20 and the depth of the concave part 24a and the like. The capacity of the reservoir part 24 can be increased or changed by changing the planar dimensions of the substrate 20, that is, the length of each side of the quadrangle and the planar dimension of the concave part 24a.

An air vent hole 22a is formed in the cover part 22 configuring the reservoir part 24. Air in the reservoir part 24 can be removed by the air vent hole 22a to allow blood to flow into the reservoir part 24. Note that, three air vent holes 22a are formed in the example shown in FIG. 3, but this number is not particularly limited. Approximately 3 to 10 air vent holes 22a can be formed. Further, the inner diameter of the air vent hole 22a can be set within the range of 0.1 μm or more and 1.0 μm or less, preferably 0.1 μm or more and 0.5 μm or less, and more preferably 0.2 μm or more and 0.5 μm or less.

As shown in FIG. 3, the concave part 24a configuring the reservoir part 24 is formed in a semicircular shape centered on point X in plan vie, as shown in FIG. 4. As shown in FIG. 5, the concave part 24a has a depth equal to or more than half the thickness of the main body part 21. As shown in FIG. 4, the inner surface 24a1 of the concave part 24a formed in a circular arc shape in plan view is formed as an inclined surface that faces obliquely upward. That is, the substrate 20 has an inclined portion between the reservoir 24 and the flow path 25. As shown also in FIG. 7, a groove 24a2 that communicates with the flow path 25 to be described later is formed on the inclined surface 24a1. The groove 24a2 has the function of flowing blood by capillary action.

As shown in FIG. 3, the flow path 25 is used for transferring the blood introduced into the introduction inlet 23 to the reservoir part 24. As shown in FIG. 4, the flow path 25 includes a concave groove 25a formed on the upper surface of the main body part 21. As shown in FIG. 5, the flow path 25 is configured by covering the upper portion of the concave groove 25a with the cover part 22. The height of the flow path 25 is the same as the height of the upper end of the reservoir part 24, and is shallower than the reservoir part 24. Therefore, a step is formed between the bottom surface 25a3 of the flow path 25 and the bottom surface 24a3 of the reservoir part 24. The step is provided with the inclined surface 24a1 described above. Accordingly, the inclined surface 24a1 gradually increases the depth of the reservoir part 24 as it moves away from the flow path 25.

As shown in FIG. 3, three flow paths 25 are formed in the substrate 20. Each of the flow paths 25 is disposed between the reservoir part 24 and the three introduction inlets 23, one end of which is connected to an introduction inlet 23, and the other end thereof is connected to the reservoir part 24. Further, the three flow paths 25 are formed in a radial shape around the aforementioned point X, and connect an introduction inlet 23 and the reservoir part 24 with the shortest distance, respectively.

Figure 6:
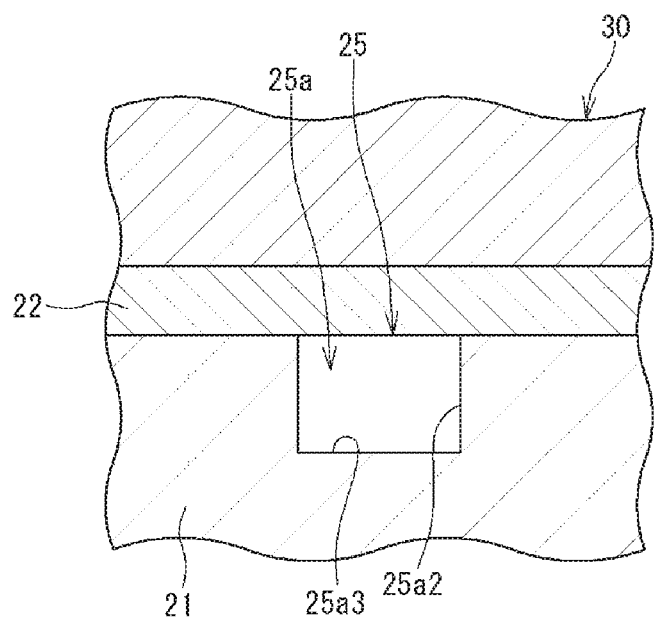
FIG. 6 is a B-B cross sectional view of FIG. 3.

As shown in FIG. 6 which is a cross-sectional view taken along line B-B cross section of FIG. 3, the flow path 25 has a bottom surface 25a3 and a side surface 25a2. The width of the bottom surface 25a3 and the height of the side surface 25a2 can be set within a range of 0.3 mm or more and 1.5 mm or less. The length of the flow path 25 also can be set within a range of 0.5 mm or more and 30 mm or less. The flow path 25 has the function of flowing blood by capillary action.

The bottom surface 25a3 and the side surface 25a2 of the flow path 25 have hydrophilic characteristic. The hydrophilic characteristic can be expressed by the magnitude of the contact angle of blood to each surface. Specifically, the bottom surface 25a3 and the side surface 25a2 of the flow path 25 are set so that the contact angle of blood exceeds 0° and is no more than 45°. Since the bottom surface 25a3 and the side surface 25a2 of the flow path 25 have hydrophilic characteristics, the capillary force by the flow path 25 is increased. In the following description, the statement "having a hydrophilic characteristic" means that the contact angle of blood exceeds 0° and is 90° or less as described above.

As shown in FIG. 5, the inner surface of the introduction inlet 23 of the substrate 20 and the bottom surface 24a3 and the inner surface 24a1 of the reservoir part 24 are also hydrophilic similar to the flow path 25. By decreasing the contact angle in the order of the introduction inlet 23, the flow path 25, and the reservoir part 24, in other words, increasing the hydrophilic characteristic in this order, the flow of blood from the introduction inlet 23 to the flow path 25 and from the flow path 25 to the reservoir part 24 can be smoothed.

The bottom surface 25a3 and the side surface 25a2 of the flow path 25, the inner surface of the introduction inlet 23, the bottom surface 24a3 and the inner surface 24a1 of the reservoir part 24 can be subjected to a treatment for enhancing hydrophilicity. For example, the surface to be processed can be subjected to etching treatment, plasma treatment, surface treatment using photocatalytic action, inorganic coating treatment such as alkali silicate, or the like. In addition, a surfactant or a hydrophilic resin may be applied to the surface to be treated. Alternatively, the surfactant may be directly kneaded to the base material 20. The hydrophilicity enhancing treatments may be applied to the upper surface of the flow path 25 and the upper surface of the reservoir part 24, that is, to the lower surface of the cover part 22. Not only the above examples, but also conventionally known treatments can be adopted as a treatment for increasing the hydrophilicity. Since the inner side surface 24a1 of the storage portion 24 is formed as an inclined surface that faces obliquely upward, when treatment for enhancing hydrophilicity, such as plasma treatment, is applied to the concave part 24a of the reservoir part 24 from above, the treatment is easily applies to the inner surface 24a of the reservoir part 24.

In order to be able to confirm the amount of blood stored in the reservoir part 24 from the outside, the cover part 22 configuring a part of the reservoir part 24 may be formed to be transparent or translucent. In this case, as shown in FIG. 3, the amount of blood in the reservoir part 24 can be understood by the scale 24b if the scale 24b is formed on the cover part 22. The cover part 22 also may be configured so that only a part of the reservoir part 24 can be visually recognized. For example, it is possible to cover the other part with an opaque cover except for a part of the cover part 22 that is formed transparent or translucent.

Cooling Body Structure

As shown in FIG. 3, the blood collection device 11 includes a cooling body 30 for cooling the flow path 25 of the substrate 20. This is due to the following reason. When blood flows out of the body, the coagulation reaction proceeds and the blood loses fluidity. Since the cross sectional area of the flow path 25 of the substrate 20 is very small, there is a high possibility that the flow path 25 will become blocked when the blood coagulates even slightly, and the blood introduced into the introduction inlet 23 cannot move to the reservoir part 24 due to the coagulation of the blood. In order to recover a small amounts of blood from the skin of the subject and store more blood in the reservoir part 24, it is necessary to ensure the flow of blood in the flow path 25 for several tens of minutes.

The inventors of the present application have observed that although the reaction rate of blood coagulation increases in an environment with an optimum temperature around body temperature, the reaction rate of blood coagulation decreases due to suppression of the action of the enzyme at a temperature lower than body temperature. The inventors considered that it would be possible to transfer a necessary amount of blood from the introduction inlet 23 to the reservoir part 24 by reducing the reaction rate of blood coagulation in the flow path 25 of the blood collection device 11. Based on this idea, the inventors of the present application provided a cooling body 30 for suppressing blood coagulation by cooling the flow path 25 to the blood collection device 11 of the present embodiment.

The cooling body 30 lowers the temperature of the blood flowing through the flow path 25 by cooling the flow path 25. Specifically, the cooling body 30 cools the flow path 25 so as to bring the blood to a temperature lower than body temperature, that is, a temperature of 4° C. to 15° C. The viscosity of the blood increases and the flow resistance in the flow path increases when the blood is cooled to less than 4° C., and the effect of suppressing blood coagulation decreases when cooled to a temperature exceeding 15° C. The cooling body 30 also maintains the blood at a temperature of 4° C. to 15° C. for 20 minutes or more.

The cooling body 30 is provided on the upper surface of the substrate 20 and is configured to cool the flow path 25 from above. In the present embodiment, the cooling body 30 is particularly provided in a range extending over the three flow paths 25 since the three flow paths 25 are provided in the substrate 20.

Figure 8:
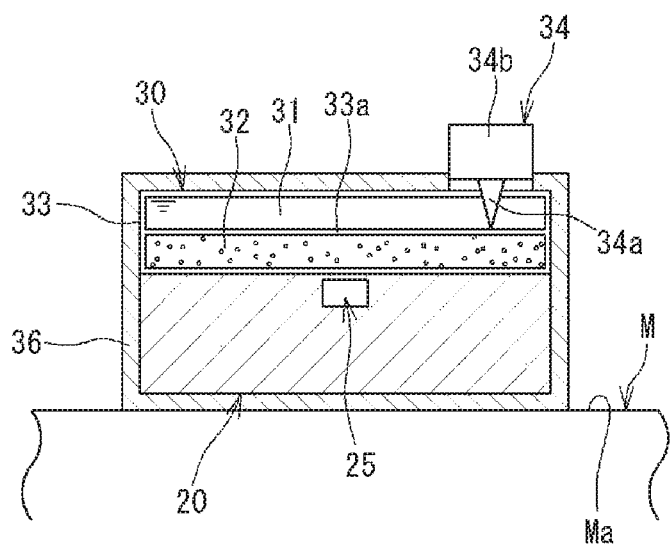
FIG. 8 is a schematic cross sectional view showing the relationship between a cooling body and the flow path of the substrate in the blood collection device.

As shown in FIG. 8, the cooling body 30 of the embodiment includes a cryogen for obtaining low temperature by mixing a plurality of substances of different kinds. For example, the cryogen is composed of water as the first substance 31 and ammonium nitrate as the second substance 32, which become a coolant by mixing them. The first substance 31 and the second substance 32 are provided in a separated state. The cooling body 30 is configured to cool the flow path 25 by mixing the first substance 31 and the second substance 32 when recovering blood from a subject. By using a cryogen as the cooling body 30, it is unnecessary to freeze the cooling body 30 in advance, and the flow path 25 can be cooled only when blood is collected.

Specifically, the cooling body 30 includes an exterior member 33 having two chambers partitioned by the separating part 33a, and the first substance 31 and the second substance 32 are stored divided into the respective chambers of the exterior member 33. The cooling body 30 further includes a mixing operation tool 34 for removing a part of the separating part 33a of the exterior member 33 to mix the first and second substances 31 and 32. The mixing operation tool 34 includes a needle 34a for making a hole in the separating part 33a and an operating part 34b for performing a hole making operation. The operating part 34b is configured by a push button and is arranged on the upper side of the substrate 20. The needle 34a protrudes downward from the lower surface of the operating part 34b, passes through the upper chamber of the exterior member 33, and faces the upper side of the separating part 33a. The needle 34a punctures the separating part 33a by pushing down on the operating part 34b so that a hole is made in the separating part 33a, thereby mixing the first substance 31 and the second substance 32.

Note that in the example shown in FIG. 8 the substrate 20 and the outer peripheral portion of the cooling body 30 are covered with a heat insulating material 36. The heat insulating material 36 suppresses heat conduction from the outside air to the cooling body 30 so that the cooling body 30 can efficiently cool the flow path 25. Particularly, the heat of the skin Ma transmitted to the substrate 20 can be suppressed since a part of the heat insulating material 36b provided on the lower surface of the substrate 20 is interposed between the skin Ma of the subject M and the substrate 20. The heat insulating material 36 may be made of a material having at least a lower thermal conductivity than the substrate 20.

Fixing Tool Structure

As shown in FIGS. 1 and 2, the fixing tool 12 is formed of a belt-like member to be wrapped around the arm or the like of the subject M. Both end parts of the fixing tool 12 are detachably attached to both end parts of the blood recovery device 11, respectively. Specifically, an adhesive layer 12a is provided at both end parts of the fixing tool 12, and the fixing tool 12 is connected to the blood recovery tool 11 by adhering the adhesive 12a to both end parts of the blood recovery device 11. The fixing tool 12 is wrapped around the subject's arm or the like and brings the lower surface of the substrate 20 of the blood collection device 11 into close contact with the skin Ma. In particular, the blood collection device 11 is fixed to the subject M so that the periphery of the lower end of the introduction inlet 23 of the blood collection device 11 closely contacts the skin Ma of the subject M.

Puncture Tool Structure

As shown in FIGS. 1 and 5, the puncture tool 13 includes a needle 13a which sticks into the skin Ma of the subject M to form micropores for blood collection, and a gripping part 13b that is held in the hand of the subject to operate the puncture tool 13. Then, the needle 13a of the puncture tool 13 is inserted from above into the introduction inlet 23 of the blood collection device 11 so that the needle 13a protrudes from the lower end of the introduction inlet 23, and pierces the skin Ma to form micropores for blood collection. Note that the puncture tool 13 need not necessarily be included in the blood collection set 10, and separately prepared puncture tools such as commercially available general-purpose puncture tool may be used.

Blood Collection Method

As described above, when the blood collection device 11 is fixed to the subject M by the fixing tool 12, the push button 34b in the mixing operation tool 34 of the cooling body 30 is pressed and the first substance 31 and the second substance 32 are mixed to create a low temperature state. Then, the puncture tool 13 is inserted into the introduction inlet 23 to pierce the skin Ma of the subject M with the needle 13a, and the blood flowing out from the skin Ma is introduced into the introduction inlet 23. In the present embodiment, since there are three introduction inlets 23 formed in the substrate 20, blood is simultaneously introduced into the three introduction inlets 23.

When the blood flowing in from the lower end opening of the introduction inlet 23 reaches the height of the flow path 25 of the introduction inlet 23, the blood enters one end of the flow path 25 by capillary action and flows into the flow path 25. The blood reaching the other end of the flow path 25 flows into the reservoir part 24 and is stored in the reservoir part 24. Coagulation is suppressed since the blood flowing through the flow path 25 is cooled by the cooling body 30. Therefore, the flow path 25 is not blocked by the coagulated blood, and the blood can be continuously transferred from the introduction inlet 23 to the reservoir part 24. Hence, an amount of blood that can be used for measurement of many examination items can be stored in the reservoir part 24. It is also possible to supply the blood stored in the reservoir part 24 for a liquid biopsy as described above.

Note that it is also conceivable to provide an anticoagulant on the inner surface of the flow path 25 in order to suppress the coagulation of blood in the flow path 25. However, in this case, the hydrophilicity in the flow channel 25 decreases, the force of blood flowing by the capillary action decreases, and the possibility of blood coagulation in the flow path 25 increases. In the present embodiment, it is possible to reliably prevent blood coagulation by increasing the hydrophilicity of the flow path 25 while cooling the blood in the flow path 25.

The introduction inlet 23 is formed in a conical shape. Therefore, the side surface of the introduction inlet 23 connected to the bottom surface 25a3 of the flow path 25 is inclined relative to the bottom surface 25a3 of the flow path 25. As a result, the flow of blood from the introduction inlet 23 to the flow path 25 becomes smooth, and the blood in the introduction inlet 23 can be reliably introduced into the flow path 25.

Figure 7:
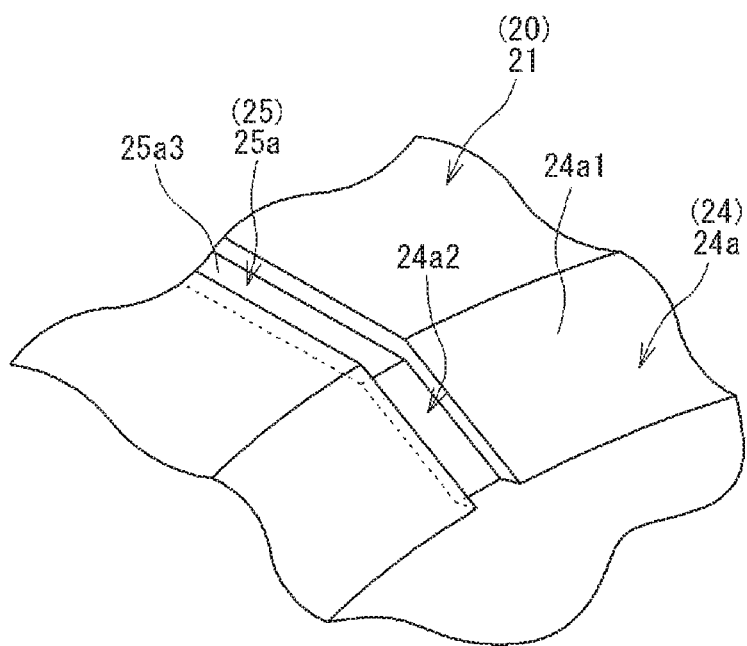
FIG. 7 is a perspective view showing the flow path and groove in the main body part of the substrate.

The blood flowing from the flow path 25 flows smoothly into the reservoir part 24 because there is scant change in the direction of the blood flow between the bottom surface 25a3 of the flow path 25, and between the inside surface 24a1 of the reservoir part 24 and substantially the bottom surface of the groove 24a2 since the inner surface 24a1 of the reservoir part 24 connected to the end of the flow path 25 is formed as an inclined surface. As shown in FIG. 7, a groove 24a2 continuing to the flow path 25 is formed on the inner surface of the reservoir part 24, and the blood flows rapidly through the groove 24a2 due to capillary action so that the blood reaches the terminal end of the flow path 25 and rapidly flows into the reservoir part 24, thereby increasing the blood collection speed.

The time required for collecting a desired amount of blood can be reduced by providing three introduction inlets 23 and three channels 25 formed in the substrate 20, and using all the introduction inlets 23 and the channels 25 to collect blood. Even if one of the flow paths 25 is blocked by blood coagulation or the like, the other flow paths 25 can be used to store the blood in the reservoir part 24. However, it is not always necessary to simultaneously use all introduction inlets 23 and the flow paths 25, inasmuch as blood may be collected using any one or two introduction inlets 23 and flow paths 25.

After storing the blood in the reservoir part 24, the fixing tool 12 is detached from the subject and the blood recovery device 11 is also removed from the fixing tool 12. The blood collection set 10 also may include an obturator that closes the hole formed in the blood collection device 11, the introduction inlet 23, and the air vent 22a. The obturator can be configured by, for example, a seal affixed so as to cover the introduction inlet 23 and the air vent hole 22a. By adhering such a seal to the introduction inlet 23 and the air vent hole 22a, it is possible to prevent blood from leaking out from the blood collection device 11.

Cooling Body Modifications

Figure 9:
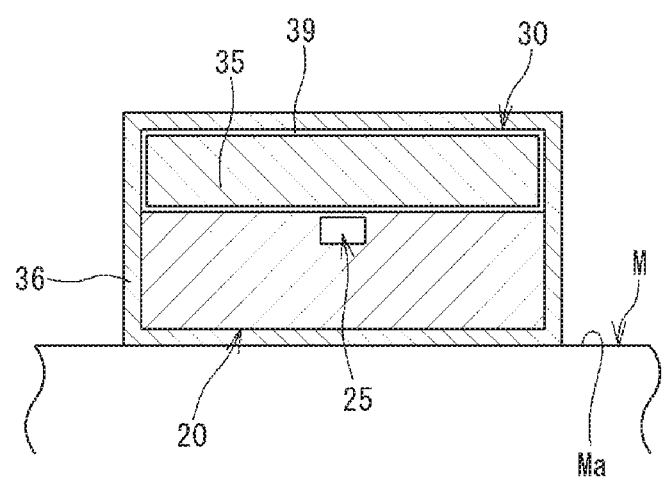
FIG. 9 is a schematic cross sectional view corresponding to FIG. 8, showing a modified example of a cooling body in the blood collection device.

FIG. 9 to FIG. 12 show modifications of the cooling body. The cooling body 30 shown in FIG. 9 is a refrigerant, and the refrigerator main body 35 containing a super absorbent resin, water and the like is housed in the exterior member 39. The refrigerant 30 is cooled by freezing or refrigerating. The refrigerant 30 may be integrated with the substrate 20 or may be a separate body. When integrated with the substrate 20, the refrigerant 30 together with the substrate 20 may be cooled by a freezer or the like. The refrigerant 30 is separate from the substrate 20, it is only necessary to cool just the refrigerant 30 in a freezer or the like, and attach the refrigerant 30 to the substrate 20 when using the blood collection device 11. The attachment of the refrigerant 30 to the substrate 20 is preferably performed by providing an adhesive layer on the lower surface of the exterior member 33 of the refrigerant 30, and attaching it to the upper surface of the substrate 20.

Figure 10:
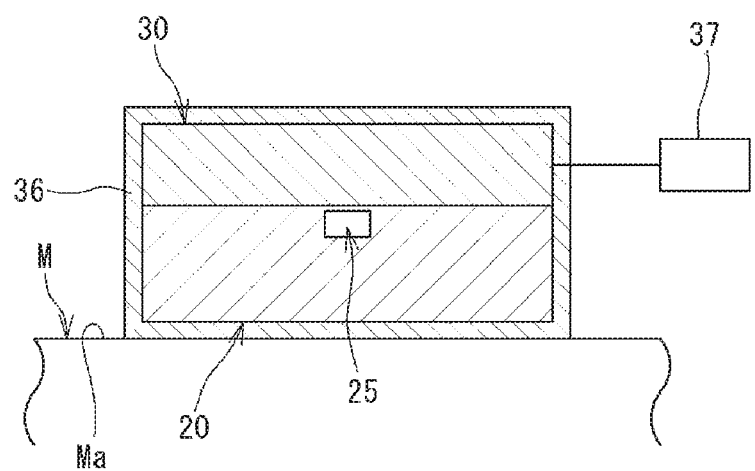
FIG. 10 is a schematic cross sectional view corresponding to FIG. 8, showing a modified example of another cooling body in the blood collection device.

The cooling body 30 shown in FIG. 10 is a Peltier element. The Peltier element 30 can obtain low temperature by Peltier effect via a flowing current. A power supply 37 is connected to the Peltier element 30, and the flow path 25 is cooled by supplying an electric current from the power source 37 before collection of blood is started to suppress coagulation of blood in the flow path 25.

Figure 11A:
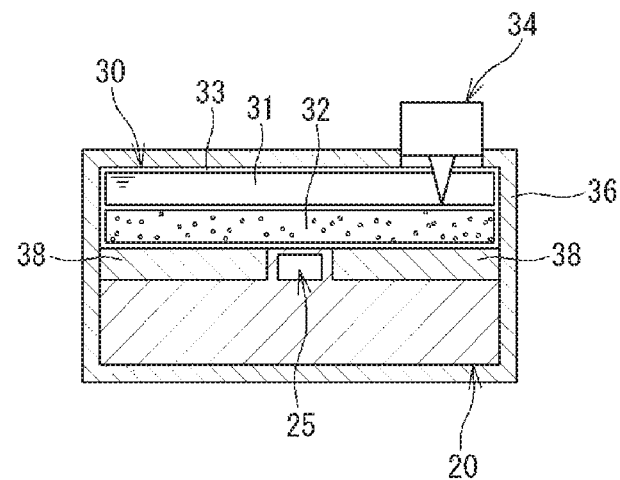
FIGS. 11A, 11B and 11C are schematic cross sectional views corresponding to FIG. 8, showing a modified example of yet another cooling body in the blood collection device.

FIG. 11 shows a cooling body 30 arranged differently from the above embodiment. FIG. 11A: the cooling body 30 is provided with the cryogens 31, 32, 33 and the heat transfer member 38 disposed on both sides in the width direction of the flow path 25 below the cryogens 31, 32, 33. The heat transfer member 38 is made of metal or the like having higher thermal conductivity than the substrate 20. In this modification, cold due to the cryogen is transferred to the heat transfer member 38 to cool the flow path 25 not only from above but also from both sides in the width direction. Therefore, it is possible to effectively suppress coagulation of blood in the flow path 25.

Figure 11B:
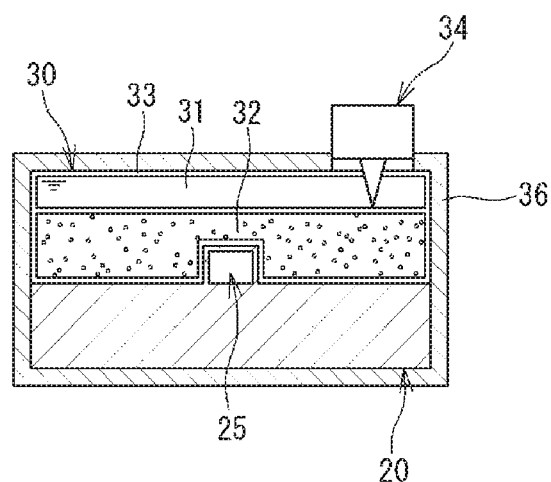

FIG. 11B shows an example in which the flow path 25 is formed so as to project upward from the substrate 20, and the cooling body 30 is provided circumscribe the upper side and both widthwise sides. Also in this modification, the flow path 25 can be cooled not only from the upper side but also from both sides in the width direction to efficiently cool the flow path 25.

Figure 11C:
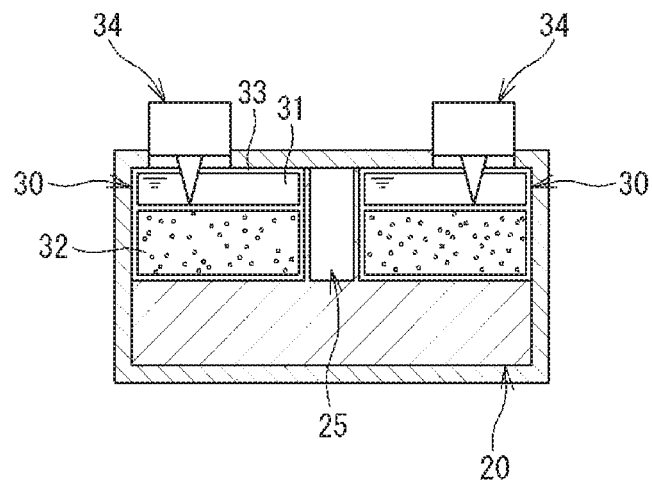

Similarly, FIG. 11C shows that the flow path 25 is formed so as to protrude upward from the substrate 20 and the cooling bodies 30 are provided on both sides in the width direction. In this example, since the cooling body 30 is provided at two locations in the width direction, a mixing operation tool 34 is provided at each location.

Figure 12:
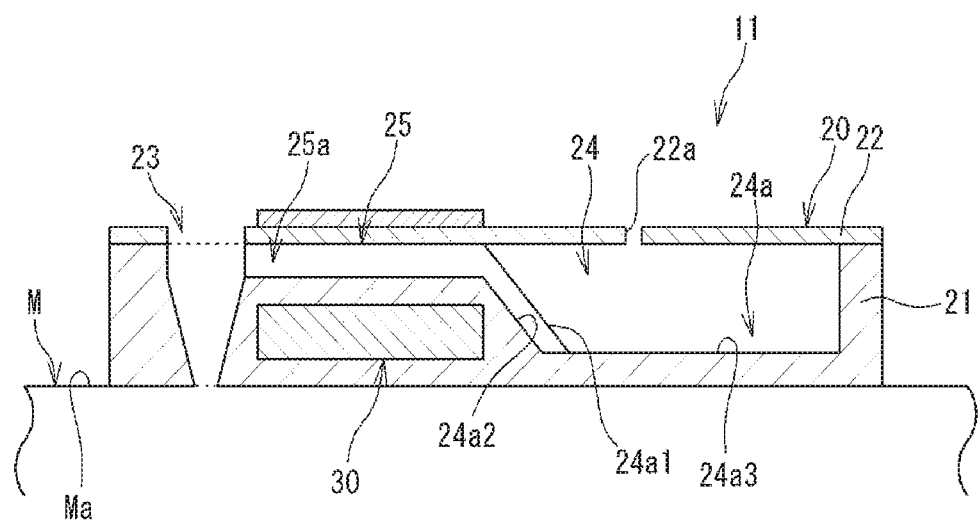
FIG. 12 is a cross sectional view showing a modified example of still another cooling body in blood collection device.

FIG. 12 shows an example in which the cooling body 30 is provided using the space between the introduction inlet 23 and the reservoir part 24 below the flow path 25 of the substrate 20. In this modified example, the blood in the flow path 25 is cooled by cooling the flow path 25 from below to suppress the coagulation of the blood.

Substrate Reservoir Part Modifications

FIGS. 13 to 19 show modifications of the reservoir part 24 of the substrate 20.

Figure 13:
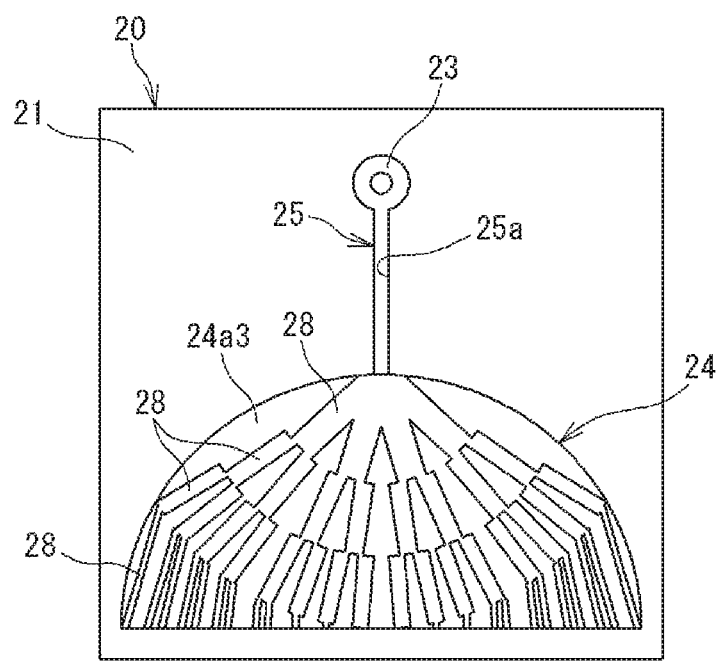
FIG. 13 is a plan view of the main body part of the substrate showing a modified example of the reservoir part in the blood collection device.

A plurality of grooves 28 are formed on the bottom surface 24a3 of the reservoir part 24 shown in FIG. 13. The plurality of grooves 28 are branched so as to spread in the width direction with the position of the flow path 25 as a base point. Each groove 28 causes blood to flow by capillary action. Therefore, the blood flowing into the reservoir part 24 from the flow path 25 is rapidly transferred in a direction away from the flow path 25 by the groove 28, so that blood is prevented from staying in the vicinity of the flow path 25. The groove width also decreases as the groove 28 moves away from the flow path 25. Therefore, as the distance from the flow path 25 increases, the capillary force increases, and the blood can be guided to a side away from the flow path 25. Accordingly, it is possible to more reliably prevent blood from staying in the vicinity of the flow path 25.

Figure 14:
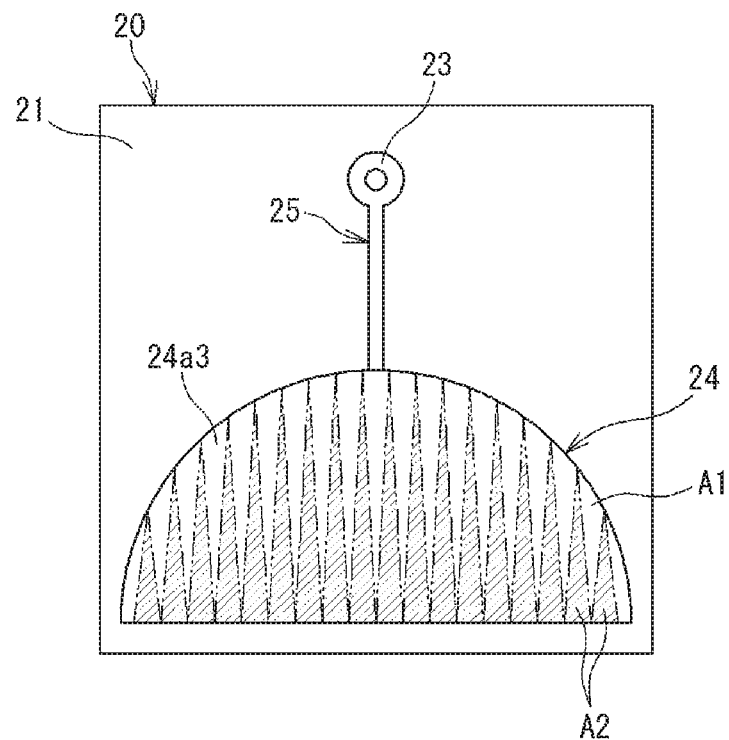
FIG. 14 is a plan view of the main body part of the substrate showing another modified example of the reservoir part in the blood collection device.

FIG. 14 shows an example in which the degree of hydrophilicity on the bottom surface 24a3 of the reservoir part 24 changes. Specifically, on the bottom surface 24a3, the degree of hydrophilicity is different between the non-hatched region A1 and the hatched region A2. The region A1 has the same hydrophilicity as the bottom surface 25a3 and the side surface 25a2 of the flow path 25. Conversely, the region A2 is more hydrophilic than the region A1. The area A1 has a large area on the side close to the flow path 25 and the area A2 has a large area on the side away from the flow path 25. That is, the hydrophilicity of the bottom surface 24a3 of the reservoir part 24 increases as it is more distant from the flow path 25. Therefore, in this modification, blood can be more smoothly guided to a region farther from the flow path 25.

Figure 15:
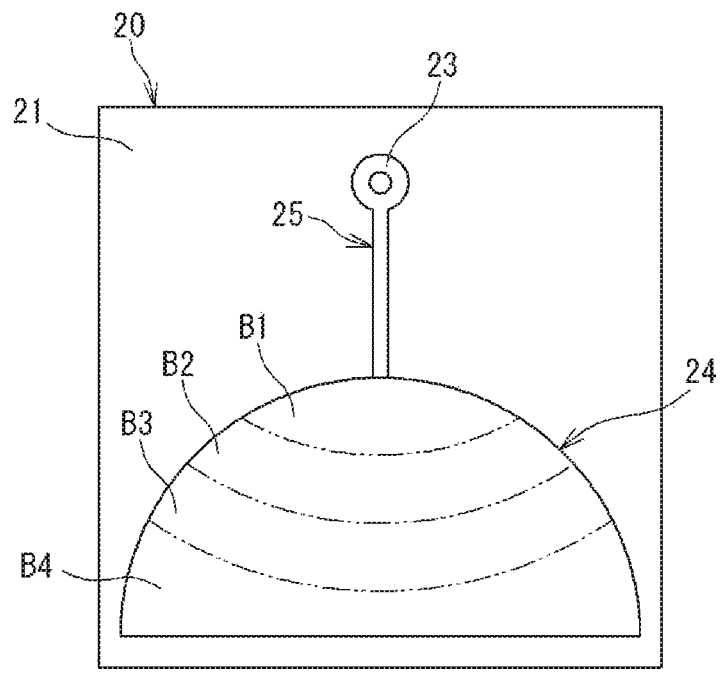
FIG. 15 is a plan view of the main body part of the substrate showing yet another modified example of the reservoir part in the blood collection device.

FIG. 15 shows an example in which the degree of hydrophilicity on the bottom surface 24a3 of the reservoir part 24 changes similar to FIG. 14. Specifically, the bottom surface 24a3 has four regions B1 to B4 partitioned by imaginary lines, and the hydrophilicity gradually increases from the region B1 nearer to the flow path 25 toward the region B4 further away from the flow path 25. Also in this modification, it is possible to smoothly guide blood to a region away from the flow path 25 since the hydrophilicity of the bottom surface 24a3 of the reservoir part 24 increases as the distance from the flow path 25 increases.

Figure 16:
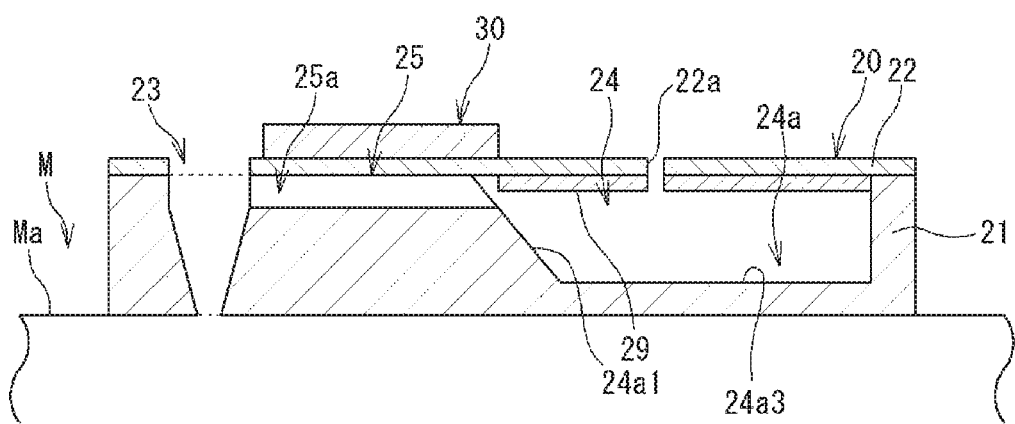
FIG. 16 is a plan view of the main body part of the substrate showing another modified example of the reservoir part in the blood collection device.

FIG. 16 shows an example in which the inner surface of a part of the reservoir part 24 has anticoagulant properties. Specifically, a sheet 29 coated with an anticoagulant is adhered to the top surface of the reservoir part 24, that is, the bottom surface of the cover part 22. Coagulation of blood in the reservoir 24 can be prevented by thus providing the anticoagulant property on the inner surface of the reservoir part 24. Note that an example in which no groove is formed on the inclined surface 24a1 of the reservoir part 24 is shown in FIG. 16.

Since the mechanism of action of the anticoagulant with respect to blood depends on its type, the anticoagulant used for the blood collection device 11 is preferably selected according to the item of the blood test. Types of anticoagulants include heparin, ethylene diamine tetraacetic acid (EDTA), sodium fluoride, sodium citrate and the like. These are defined as anticoagulants used according to test items such as blood gas test, biochemical test, blood glucose test, hemoglobin test, coagulation test, erythrocyte test and the like. Therefore, it is sufficient to prepare the blood collection device 11 coated with the anticoagulant according to the type of examination prior to the examination, and select the blood collection device 11 to be used according to the type of examination to be performed. In addition, it is possible to manufacture the substrate 20 according to the type of inspection by adhering the sheet 29 coated with anticoagulants of different types into the reservoir part 24.

Figure 17:
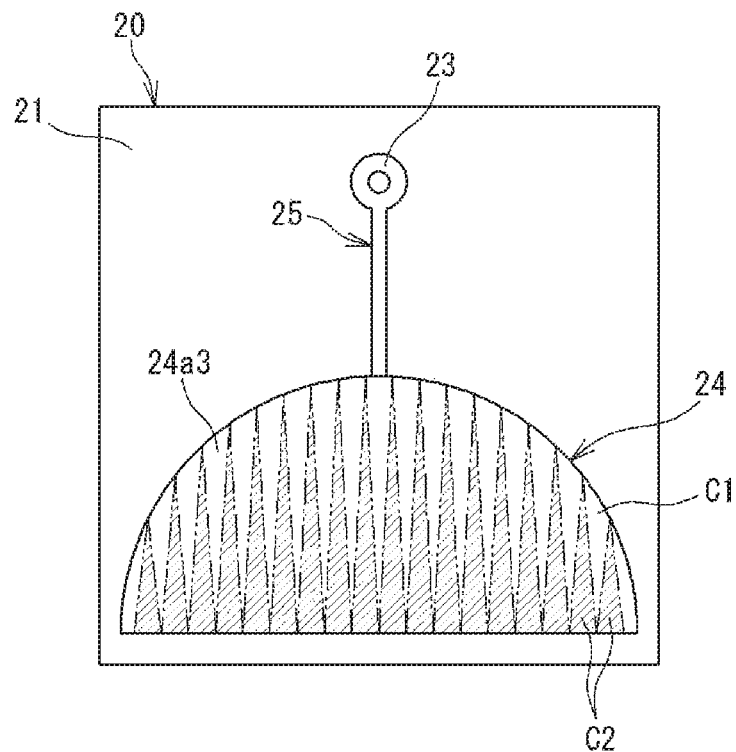
FIG. 17 is a plan view of the main body part of the substrate showing another modified example of the reservoir part in the blood collection device.

FIG. 17 shows an example in which the inner surface of a part of the reservoir part 24 has anticoagulant and hydrophilic properties. Specifically, the non-hatched region H1 is a region having hydrophilicity, and the hatched region C2 is the region having anticoagulant property on the bottom surface 24a3 of the reservoir part 24. The region C1 becomes smaller going away from the flow path 25, and the region C2 becomes larger going away from the flow path 25. Therefore, the hydrophilicity of the bottom surface 24a3 of the reservoir part 24 increases as the bottom surface 24a3 is closer to the flow path 25, and the anticoagulability increases as the bottom surface 24a3 is farther from the flow path 25.

In this way, hydrophilicity is higher closer to the flow path 25, and the easier it is for the blood flowing out from the flow path 25 to flow into the storage part 24, whereas the anticoagulability is higher farther from the flow path 25, so that it is possible to prevent the blood stored in the region distant from the flow path 25 from coagulating.

Figure 18:
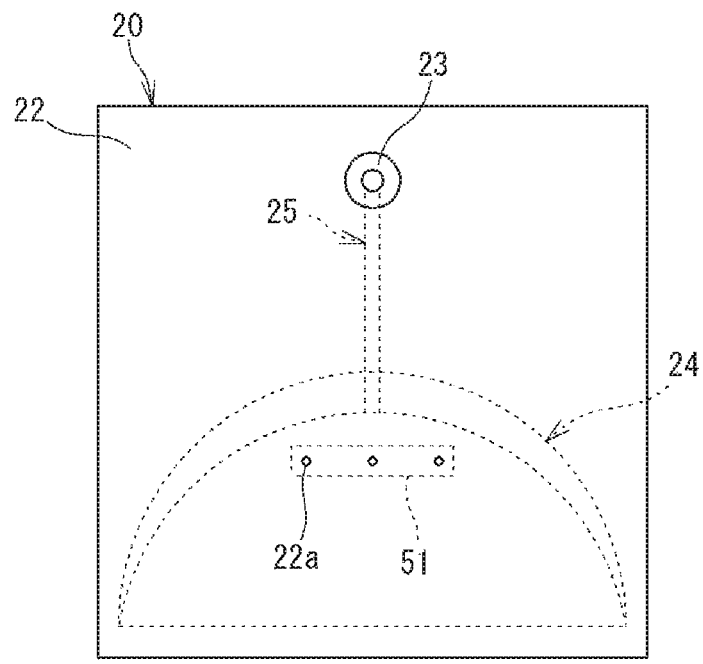
FIG. 18 is a plan view of the main body part of the substrate showing still another modified example of the reservoir part in the blood collection device.
Figure 19:
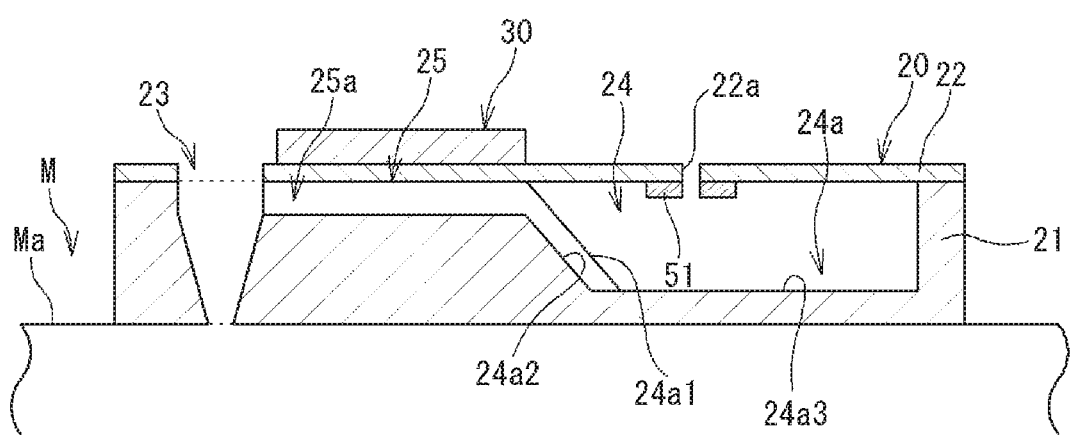
FIG. 19 is a cross sectional view of the blood collection device of FIG. 18.

FIGS. 18 and 19 show an example in which the periphery of the air vent hole 22a formed in the reservoir part 24 is hydrophobic. Specifically, a treatment for increasing hydrophobicity is applied to the periphery of the air vent hole 22a on the bottom surface of the cover part 22. As a treatment for enhancing the hydrophobicity, a sheet 51 having a higher hydrophobicity than the cover part 22 is attached to the bottom surface of the cover part 22. It is possible to prevent blood from flowing out of the blood collection device 11 from the air vent hole 22a because the periphery of the air vent hole 22a is hydrophobic.

Substrate Introduction Inlet Modifications

Figure 20:
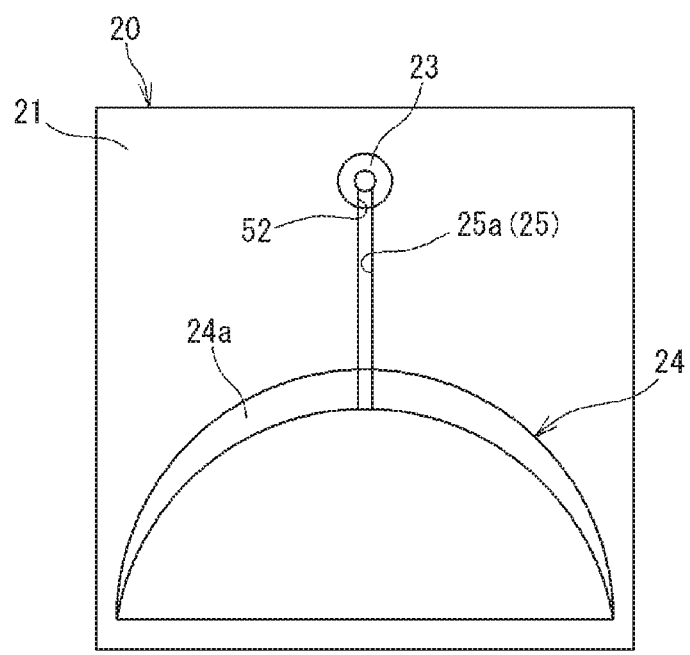
FIG. 20 is a plan view of the main body part of the substrate showing a modified example of the introduction inlet in the blood collection device.
Figure 21:
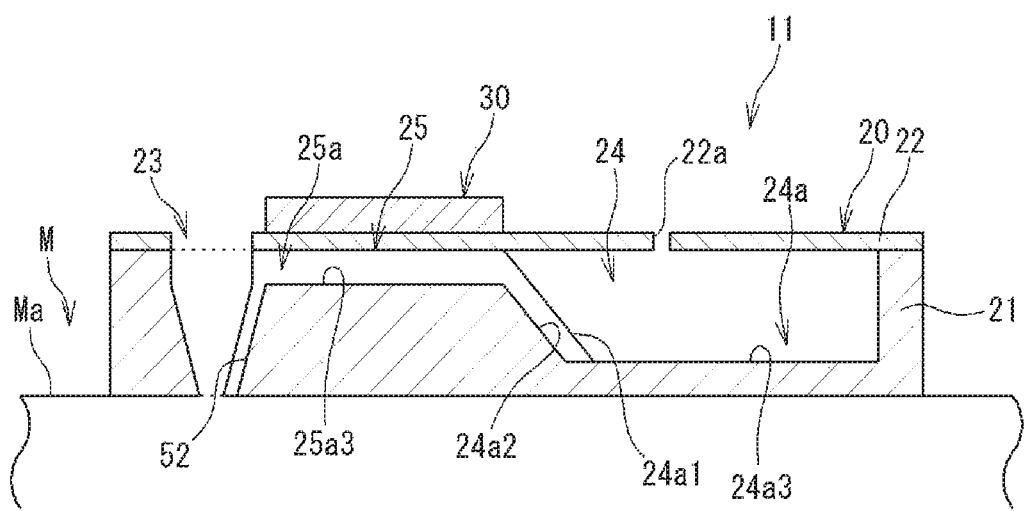
FIG. 21 is a cross sectional view of the blood collection device of FIG. 20.

FIGS. 20 to 21 show modifications of the introduction inlet 23 of the substrate 20. A groove 52 for flowing blood by capillary action is formed on the inner surface of the introduction inlet 23. One end of this groove 52 is connected to the flow path 25 and the other end reaches the bottom end of the introduction inlet 23. The blood introduced into the introduction inlet 23 flows through the groove 52 by capillary action, and flows into the flow path 25. Therefore, it is possible to rapidly flow the blood from the introduction inlet 23 to the flow path 25.

Substrate Modifications

Figure 22:
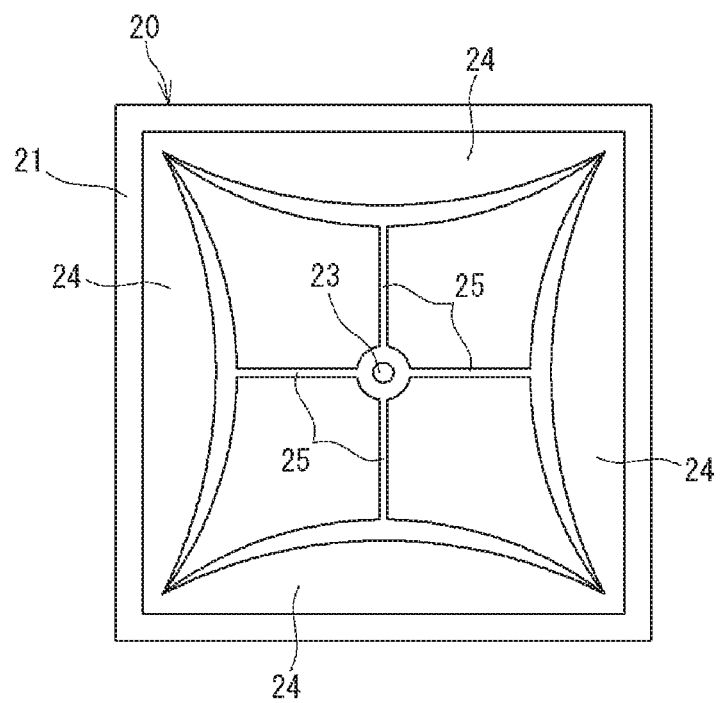
FIG. 22 is a plan view of the main body part of the substrate showing a modified example of the substrate in the blood collection device.
Figure 23:
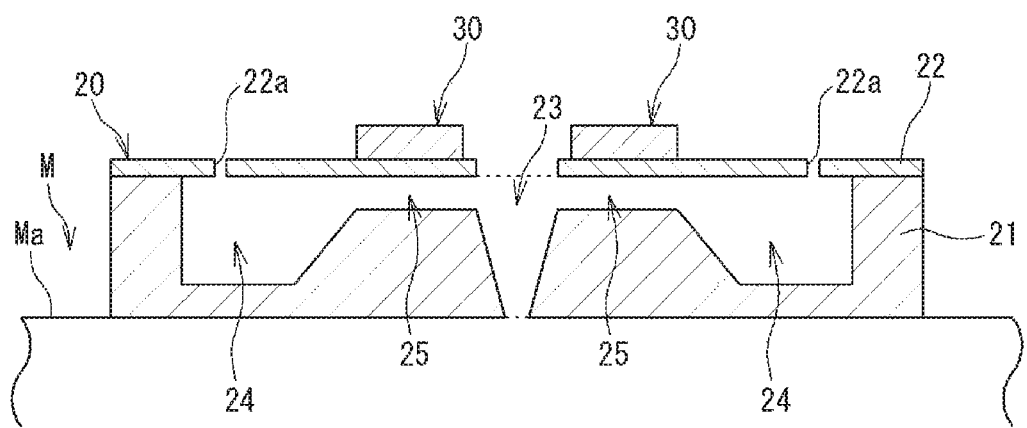
FIG. 23 is a cross sectional view of the blood collection device of FIG. 22.

FIGS. 22 to 25 show modifications of the substrate 20. The introduction inlet 23 shown in FIGS. 22 and 23 is formed at the center of the surface of the substrate 20, and the reservoir part 24 is formed on the outer peripheral side of the substrate 20 so as to circumscribe the introduction inlet 23. Four flow paths 25 extend from the introduction inlet 23 in a cross shape and are connected to the reservoir part 24, respectively. According to this modification, blood can be suitably stored in the reservoir part 24 even when, for example, the direction of the blood collection device 11 attached to the arm changes due to the movement of the arm since the storage portion 24 is formed on the entire circumference of the substrate 20.

Figure 24:
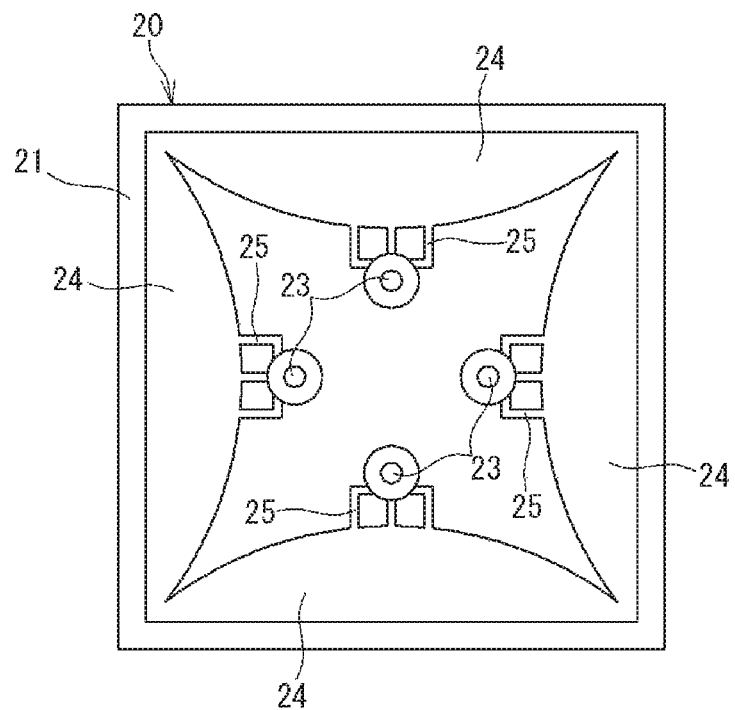
FIG. 24 is a plan view of the main body part of the substrate showing another modified example of the substrate in the blood collection device.
Figure 25:
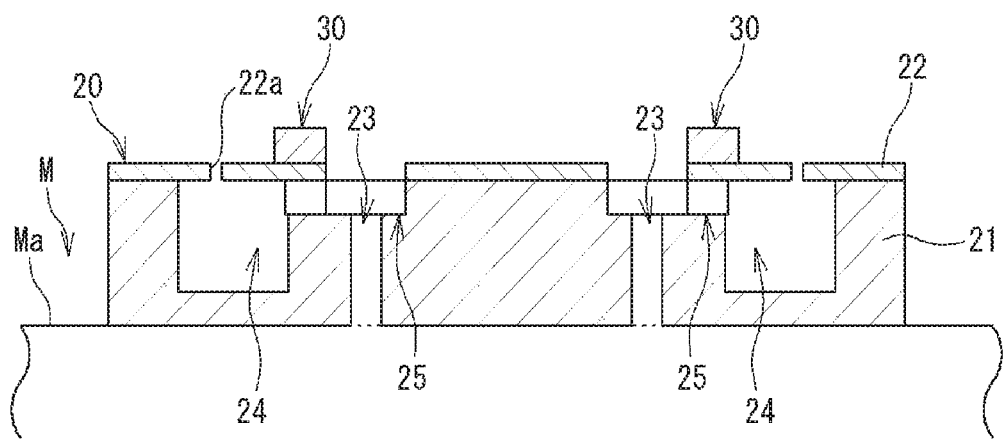
FIG. 25 is a cross sectional view of the blood collection device of FIG. 24.
Figure 26:
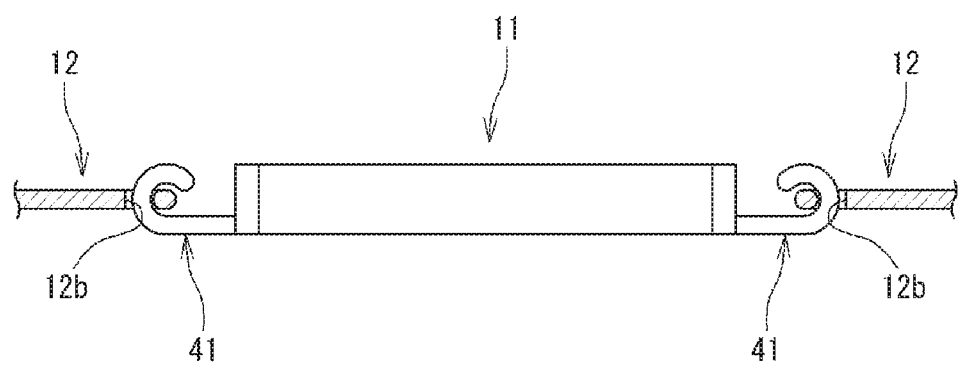
FIG. 26 is a cross sectional view showing a modification of the fixing tool.

The substrate 20 shown in FIGS. 24 and 25 has the reservoir part 24 formed all around the outer circumference of the substrate 20, and four introduction inlets 23 are formed inside the reservoir part 24. Three flow paths 25 are formed between each introduction inlet 23 and the reservoir part 24 in the vicinity thereof. The blood introduced into each introduction inlet 23 flows through the flow path 25 and is stored in the reservoir part 24. In this modification it is possible to appropriately store the blood in the reservoir part 24 even if the direction of the blood collection device 11 changes due to the movement of the arm similar to the modification shown in FIGS. 22 and 23. In addition, even if one of the flow paths 25 and the introduction inlets 23 is blocked by blood coagulation, the other flow path 25 and the introduction inlets 23 can be used to collect blood since a plurality of introduction inlets 23 are formed and a plurality of flow paths 25 also are formed.

Fixing Tool Modifications

FIGS. 26 to 30 show modifications of the fixing tool 12. The fixing tool 12 shown in FIG. 26, has engagement holes 12b formed at both ends. Engagement hooks 41 provided at both end parts of the blood collection device 11 engage with the engagement holes 12b, and the fixing tool 12 is coupled to the blood collection device 11 by this engagement. After collecting the blood, the fixing tool 12 can be removed from the blood collection device 11 by removing the engagement hook 41 from the engagement hole 12b.

Figure 27:
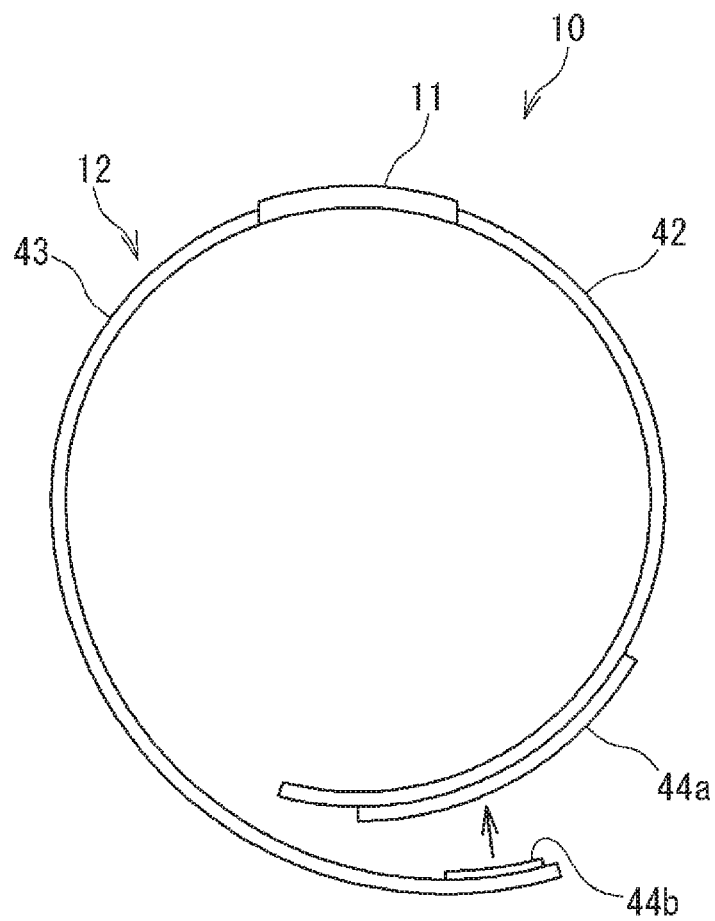
FIG. 27 is a side view showing another modification of the fixing tool.

The fixing tool 12 shown in FIG. 27 is configured by two divided bodies 42 and 43 that are divided in the longitudinal direction, one end in the longitudinal direction of one divided body 42 is connected to one side part of the blood collection device 11, and one end in the longitudinal direction of the other divided body 43 is connected to the other side portion of the blood collection device 11. A pair of hook-and-loop fasteners 44a and 44b are attached to the other end of one divided body 42 and the other end of the other divided body 43, and the pair of hook and loop fasteners 44a and 44b are wound around the arm or the like so that the fixing tool 12 can be attached to the arm. In this modification, the winding length of the fixing tool 12 can be adjusted according to the thickness of the arm or the like so that the blood collection device 11 can be reliably fixed to the arm or the like.

Note that instead of the pair of hook-and-loop fasteners 44a and 44b in FIG. 27, it is also possible to adopt a combination of, for example, magnet and magnet, or a combination of a magnet and a magnet body such as iron or the like that are mutually adhered by magnetic force.

Figure 28:
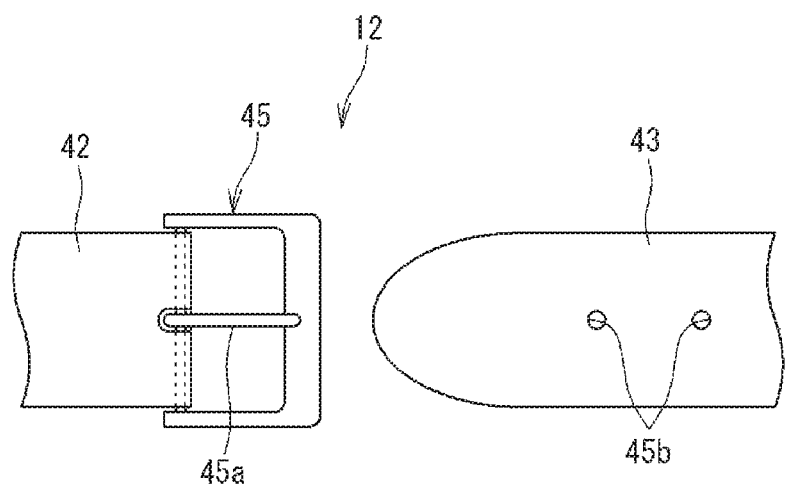
FIG. 28 is an enlarged view of the essential part showing another modification of the fixing tool.

The fixing tool 12 shown in FIG. 28 has a pin buckle 45 at the end of one divided body 42, and a plurality of holes 45b into which the pin 45a of the pin buckle 45 is inserted is formed at the end of the other divided body 43. The winding length of the fixing tool 12 can be adjusted according to the thickness of the subject's arm or the like, and the blood collection device 11 can be securely fixed to the arm by selecting one of the plurality of holes 45b and inserting the pin 45a.

Figure 29:
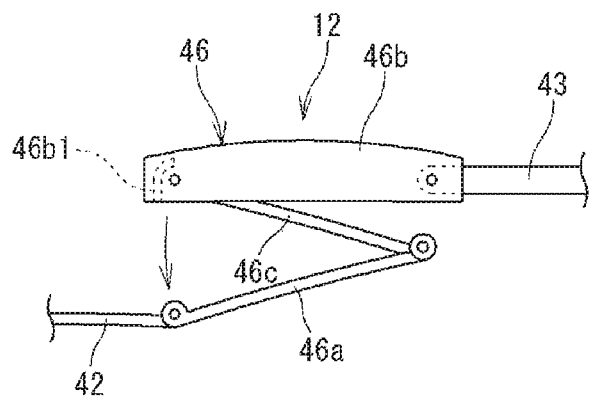
FIG. 29 is an enlarged view of the essential part showing yet another modification of the fixing tool.

The fixing tool 12 shown in FIG. 29 is provided with a one-way type buckle 46 which includes a first arm 46a having one end oscillatably connected to an end part of one of the divided bodies 42, a buckle body 46b having one end oscillatably connected to the other divided body 43, and a second arm 46c having both ends oscillatably connected to the other end of the first arm 46a and the other end of the buckle main body 46b. The first arm 46a, the second arm 46c, and the buckle main body 46b are folded so as to overlap, and a locking metal fitting 46b1 of the buckle main body 46b is engaged with one end of the first arm 46a, so that the fixing tool 12 can be wound around an arm or the like and be fixed. The fixing tool 12 also can be easily attached to and detached from the arm or the like by opening the first arm 46a, the second arm 46c, and the buckle body 46b.

Figure 30:
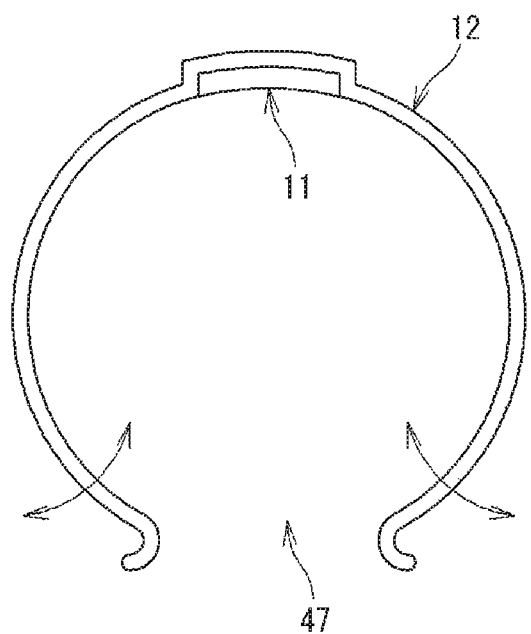
FIG. 30 is a side view showing still another modification of the fixing tool.

The fixing tool 12 shown in FIG. 30 is formed in a substantially u-shaped curve, and a gap 47 is formed between both end parts. The blood collection device 11 is detachably mounted to an intermediate part of the fixing tool 12. The fixing tool 12 is formed of an elastically deformable synthetic resin or the like. The interval 47 is set to be smaller than the thickness of the arm or the like of the subject to whom the blood collection device 11 is attached, and the arm or the like can be inserted in the interval 47 by elastically deforming the fixing tool 12 so as to enlarge the interval 47, and the fixing tool 12 can be fitted to the arm or the like by elastically restoring the fixing tool 12 so as to narrow the interval 47.

Blood Collection Set Modifications

Figure 31A:
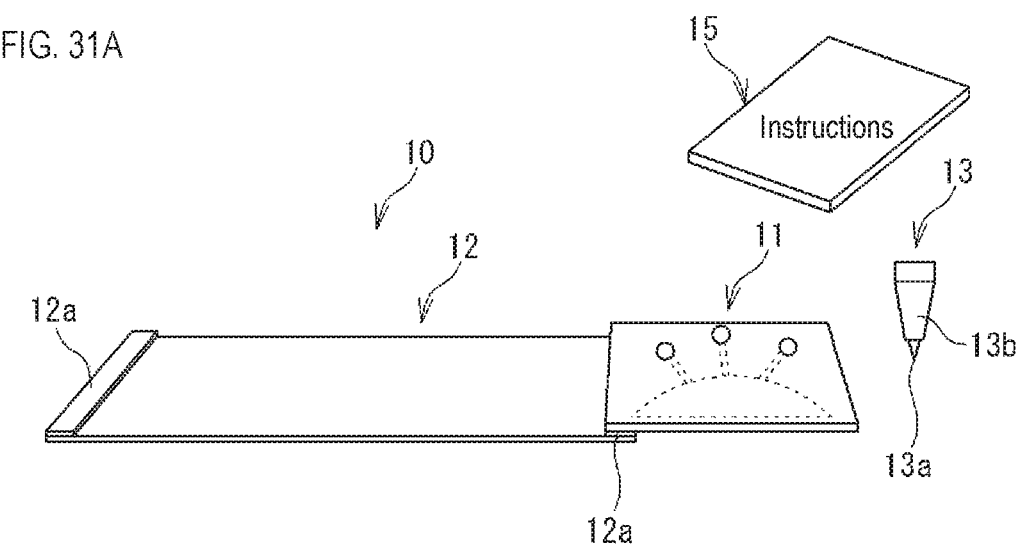
FIGS. 31A and 31B are perspective views showing a modification of the blood collection set.
Figure 31B:
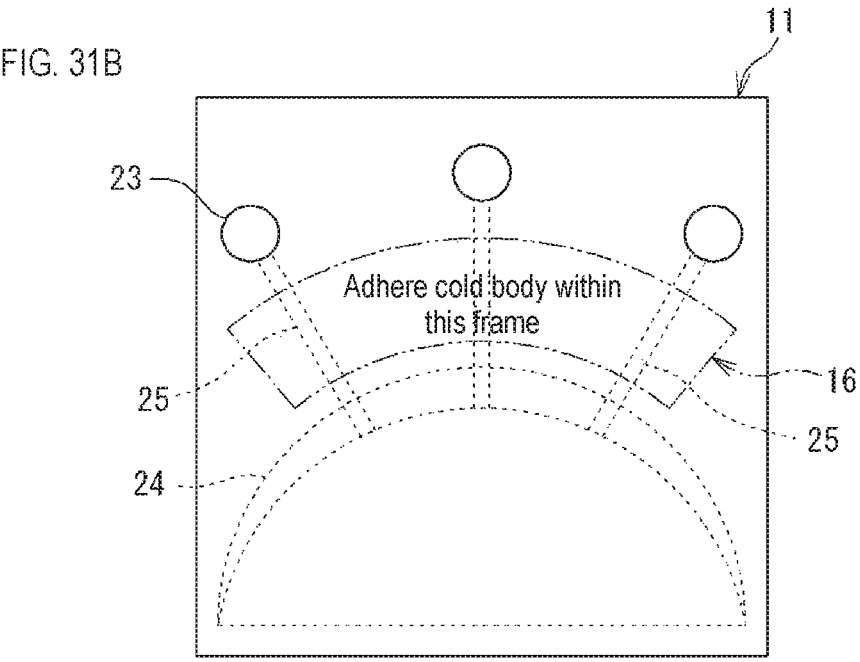

FIG. 31 shows a modification of the blood collection set. This blood collection set includes instructions 15. In addition, the blood collection device 11 of the blood collection set 10 does not have the cooling body as described above, and is configured only by the substrate. The blood collection device 11 is configured to cool the flow path by mounting a commercially available cooling body prepared by the user him/herself.

The instructions 15 is an information medium which records instructions for cooling the flow path of the blood collection device 11. The instructions 15 is, for example, an explanation of the type of cooling body that can be used for cooling the flow path, an explanation of the method of using the cooling body and the like. The user can appropriately cool the flow path and collect the blood by reading the instructions 15.

As shown in FIG. 31A, the location for mounting the cooling body is indicated by a frame 16 on the upper surface of the blood collection device 11, and an instruction is recorded to indicate that is the location at which the cooling body is to be adhered. This instruction is also one of the instruction information for cooling the flow path, and the blood recovery device 11 itself is the information medium.

The cooling body also may be provided as a dedicated product for the blood collection device 11, or a commercially available general-purpose product also may be used. In any case, the instruction 15 describes the type of cooling body that can be used. Instruction 15 records not only a description concerning the cooling body, but also the overall usage method of the blood collection set 10.

The information medium on which the instruction to cool the flow path is recorded is not limited to a paper medium on which the instruction information is printed as described in instruction 15, inasmuch as the instruction information may be, for example, electronic data such as character data, audio data, video data recorded on an electromagnetic storage medium such as a CD-ROM, a DVD-ROM, a flash memory or the like, and this electromagnetic recording medium may be included in the blood collection set 10. The information medium may be a product package containing the blood collection device 11.

Verification Test 1

In order to verify the effectiveness of the present invention, the inventors conducted verification experiments. In this verification test, control blood was caused to flow out from a simulated blood vessel, blood was collected by blood collection devices according to the embodiment and the comparative example, and the amount of control blood that was recovered was measured.

Blood Collection Device

Figure 32:
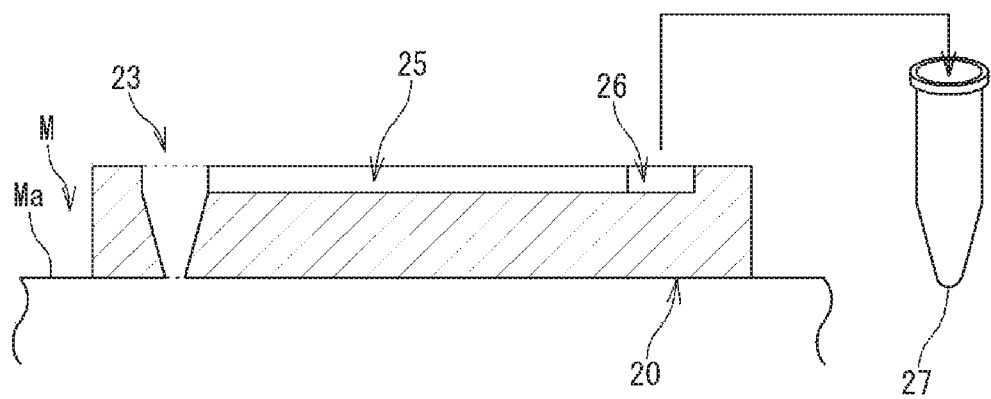
FIG. 32 is a cross sectional view of the blood collection device used in a verification test.
Figure 33:
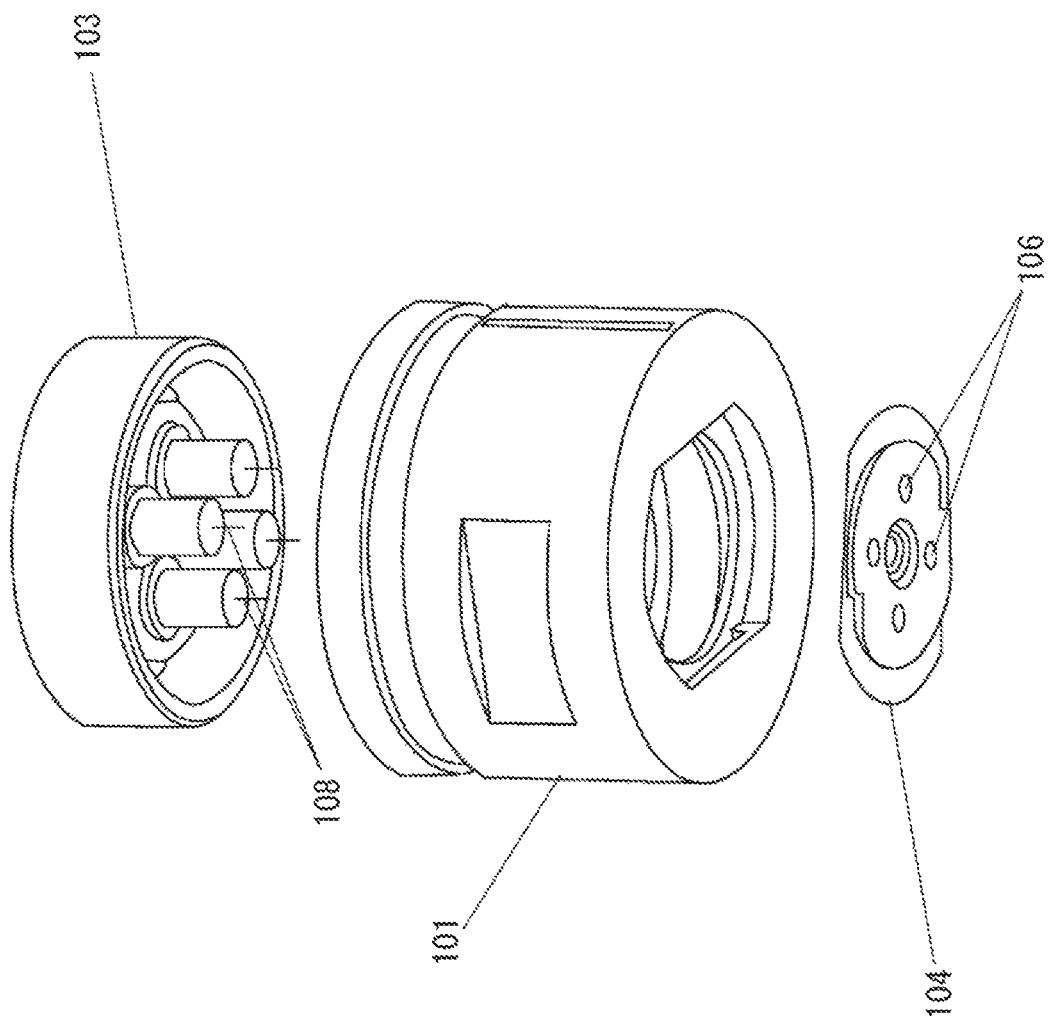
FIG. 33 is an exploded perspective view showing a conventional blood collection device.
Figure 34:
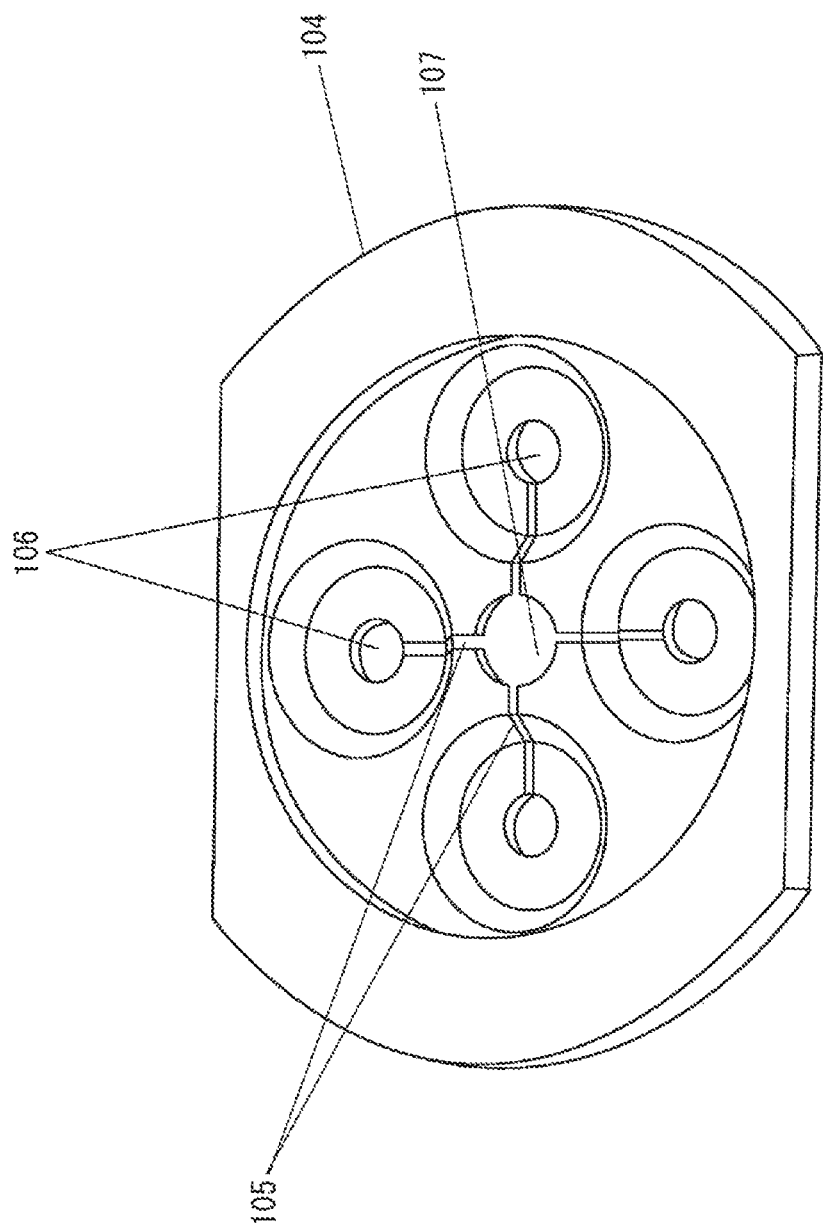
FIG. 34 is a perspective view showing a conventional blood collection device.
Figure 35:
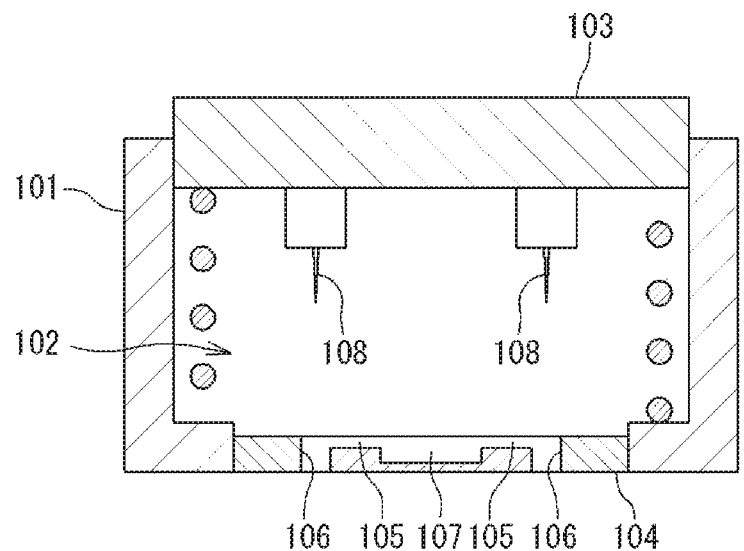
FIG. 35 is a cross sectional view showing a conventional blood collection device.

As shown in FIG. 32, the blood collection device used in the verification test 1 was produced by forming a flow path 25, and an introduction inlet 23 connected to one end of the flow path 25, on a substrate 20 made of polymethylmethacrylate resin (PMMA). An outflow port 26 for transferring blood to a blood storage container 27, which is a substitute for the above-mentioned reservoir part, was formed at the other end of the flow path 25. The introduction inlet 23 was a conical hole through the substrate 20. The flow path 25, the introduction inlet 23, and the outflow port 26 of the substrate 20 were each subjected to a hydrophilization treatment by ultraviolet irradiation. For this hydrophilization treatment, UV/Ozone cleaner model UV-1 manufactured by Samco Co., Ltd. was used. Thrombin was pre-applied to the flow path 25 of the substrate 20 so as to promote the coagulation of the control blood.

In the blood collection device of the embodiment, a Peltier element was used as a cooling body, and the flow path 25 was cooled so that the blood in the flow path 25 was adjusted to 7° C. The blood collection device of the comparative example was the same as the example except that it was not cooled by the Peltier element.

Control Blood

The control blood used was manufactured by mixing 1000 μL of control blood LC-TROL 8 (serial number: 3014062996, Lot No. 151207 N) manufactured by Nitto Seisakusho Co., Ltd., 400 μL standard human plasma for blood coagulation test (Lot No. 503248) manufactured by Sysmex Corporation, and 600 μL of buffer solution supplied with the fibrinogen kit Trombocheck Fib manufactured by Sysmex Corporation.

Simulated Blood Vessel

A simulated blood vessel was manufactured by forming micropores having a diameter of 1 mm in a silicone tube manufactured by Q & S Co., Ltd. having an inner diameter of 3 mm and an outer diameter of 6.5 mm using a biopsy Trepan BP-10F manufactured by Igarashi Medical Industry Co., Ltd., and a syringe pump was connected to one end of the silicone tube, and the other end of the tube was occluded with a clip. The control blood was introduced into the silicon tube by the syringe pump, and the flow rate of the control blood flowing through the simulated blood vessel was adjusted so that the control blood flowed out from the micropores while forming droplets.

Blood Collection

Control blood was flowed into the simulated blood vessel at a flow rate of 20 μL/min at room temperature of 25° C., and after it was confirmed that the blood flowed out from the micropores, the blood flowing out of the simulated blood vessel was collected for 6 minutes by the blood collection device of the embodiment and the comparative example. The assumed blood volume recovered with a recovery time of 6 minutes is 120 μL.

The amount of blood that could be recovered by the blood collection device of the comparative example was 50 μL. In the blood collection device of the comparative example, the control blood coagulated and it was difficult to recover the assumed amount of blood. In contrast, the amount of blood that could be collected in the blood collection device 11 of the embodiment was 106 μL. That is, the blood collection device 11 of the embodiment was able to collect about twice as much blood volume as the blood collection device 11 of the comparative example. In the blood collection device 11 of the embodiment, the coagulation of the blood was suppressed by the cooling of the flow path 25, and it was possible to collect an amount of blood close to the assumed blood volume.

Verification Test 2

Although the blood collection amount was verified for a relatively short time of 6 minutes was in verification test 1 described above, whether a large amount of blood could be collected was verified in verification test 2. The blood collection device and simulated blood vessel used for the test were the same as used in verification test 1. The collection of blood was performed by allowing control blood to flow into the simulated blood vessel at a flow rate of 50 μL/min, and blood was collected for 20 minutes by the blood collection device of the embodiment and the blood collection device of the comparative example.

The assumed blood volume collected with a recovery time of 20 minutes is 1 mL. The amount of blood that could be collected by the blood collection device 11 of the comparative example was 0.05 mL. In the comparative example, due to the coagulation of control blood, the amount of blood that could be collected did not reach the assumed amount by a large margin. In contrast, the amount of blood that could be collected in the blood collection device 11 of the embodiment was approximately 1 mL. Therefore, it is understood that it is possible to collect almost the assumed amount of blood even if the collection time is longer by using the blood collection device of the embodiment, and the blood collection device of the embodiment is effective for collecting a large amount of blood.

The above embodiment and its modifications are to be considered in all respects as illustrative and not restrictive. The scope of the invention is defined solely by the scope of the claims and not by the forgoing description, and may be variously and appropriately modified insofar as such modification is within the scope of the meaning expressed in the claims.

For example, although the substrate 20 of the blood collection device 11 is made of a material that is elastically deformable along the arm or the like of the subject in the above-described embodiment, the substrate also may be formed of a hard material that does not undergo elastic deformation. In this case, the substrate 20 does not elastically deform along the skin of the subject, but the skin adheres closely to the lower face side of the substrate 20 since the skin of the subject is deformed along the substrate 20.

The planar shape of the substrate 20 is not limited to a quadrilateral shape and may be formed in a circular shape such as a polygonal shape other than a quadrangular shape, a true circle, an ellipse, an oblong shape, or the like.

The shape of the reservoir part 24 formed on the substrate 20 of the blood collection device 11 is not particularly limited insofar as it can store the blood flowing in from the flow path 25. For example, the reservoir 24 of the above embodiment has a semicircular planar shape, but it is not limited such, and may be formed into a polygon such as a triangle, a quadrangle or the like, or any other arbitrary shape. The blood collection device 11 of the present invention need not be provided with the reservoir part 24 inasmuch as the blood flowing from the terminal end of the flow path 25 also may be collected by aspirating with a syringe pipe or the like.

The shape of the flow path 25 formed in the substrate 20 of the blood collection device 11 is not particularly limited insofar as blood can flow from the introduction inlet 23 to the reservoir part 24 by utilizing capillary force. For example, in the above-described embodiment, the flow path 25 is formed in a quadrangular cross section, but may be a polygonal shape other than a quadrangular shape or a circular shape. In the case of a circular shape, it is preferable to set the inner diameter to 0.3 mm or more but not more than 1.5 mm.

The puncture tool 13 may be configured to simultaneously operate the mixing operation tool 34 of the cooling body 30 when inserting the puncture tool 13 into the introduction inlet 23 of the substrate 20 to form a hole in the skin. In this way it is possible to prevent forgetting to cool down and blood coagulation in the flow path can be reliably suppressed.

What is claimed is:

1. A blood collection device comprising:
   a substrate which has an introduction inlet for introducing blood of a subject;
   a reservoir part configured to collect the blood;
   a flow path connecting the introduction inlet and the reservoir part, and configured to allow the blood to flow into the reservoir part by capillary action;
   a cooling body provided beside the flow path, the cooling body further including:
      a first chamber having a first substance; and
      a second chamber having a second substance that is different from the first substance; and
   a separating part configured to partition between the first chamber and the second chamber,
   wherein the cooling body is configured to cool the flow path by penetrating the separating part with a needle to mix the first substance and the second substance.

2. The blood collection device according to claim 1, wherein the cooling body comprises at least one of a refrigerant, a cryogen, or a peltier element.

3. The blood collection device according to claim 2, further comprising:
   the first substance comprising a cryogen containing liquid component;
   the second substance comprising a solid component.

4. The blood collection device according to claim 1, wherein the cooling body cools the flow path so as to bring the blood in the flow path to a temperature of 4° C. to 15° C.

5. The blood collection device according to claim 1, wherein an internal diameter of the flow path is 0.3 mm to 1.5 mm.

6. The blood collection device according to claim 1, wherein the flow path has hydrophilic properties.

7. The blood collection device according to claim 1, wherein the flow path is treated to have hydrophilicity by etching treatment or plasma treatment.

8. The blood collection device according to claim 1, wherein a cross-sectional area of the flow path is smaller than a surface area of an opening of the introduction inlet.

9. The blood collection device according to claim 1, wherein the reservoir part has a capacity of at least 1.0 m or more.

10. The blood collection device according to claim 1, wherein the substrate comprises:
    an inclined part connected to a bottom surface of the flow path and a bottom surface of the reservoir part and is inclined downward from the flow path toward the reservoir part.

11. The blood collection device according to claim 10, wherein the inclined part has a groove connected to the flow path.

12. The blood collection device according to claim 11, wherein at least part of an inner surface of the reservoir part has anticoagulant properties.

13. The blood collection device according to claim 12, wherein a sheet coated with an anticoagulant is provided at least in part of the inner surface of the reservoir part.

14. The blood collection device according to claim 11, wherein at least part of an inner surface of the reservoir part has hydrophilic properties.

15. The blood collection device according to claim 14, wherein the hydrophilic properties of the inner surface of the reservoir part increases as a distance from the flow path increases.

16. The blood collection device according to claim 14, wherein
    the hydrophilic properties of the at least part of the inner surface of the reservoir part increases as the at least part of the inner surface of the reservoir part nears the flow path, and an anticoagulation property of the at least part of the inner surface of the reservoir part increases as the at least part of the inner surface of the reservoir part is farther from the flow path.

17. The blood collection device according to claim 11, wherein at least a part of an inner surface of the reservoir part has a groove with a width that becomes narrower when the groove becomes farther from the flow path.

18. The blood collection device according to claim 11, wherein the reservoir part has an air vent hole.

19. The blood collection device according to claim 11, wherein
    the flow path is extending between the introduction inlet and the reservoir part in a lateral direction, and
    the cooling body is provided above or beneath the flow path.

* * * * *